United States Patent
Hashimoto et al.

(10) Patent No.: US 11,952,620 B2
(45) Date of Patent: Apr. 9, 2024

(54) NUCLEIC ACID DETECTION OR QUANTIFICATION METHOD, CHIP AND ASSAY KIT THEREFOR, DEVICE FOR DETECTING OR QUANTIFYING NUCLEIC ACID AND PROGRAM THEREFOR

(71) Applicant: KABUSHIKI KAISHA TOSHIBA, Tokyo (JP)

(72) Inventors: Koji Hashimoto, Atsugi (JP); Keiko Ito, Kawasaki (JP); Mika Inada, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 238 days.

(21) Appl. No.: 17/095,139

(22) Filed: Nov. 11, 2020

(65) Prior Publication Data

US 2021/0079457 A1    Mar. 18, 2021

Related U.S. Application Data

(62) Division of application No. 15/907,700, filed on Feb. 28, 2018, now Pat. No. 10,865,438.

(30) Foreign Application Priority Data

Jun. 16, 2017  (JP) ................. 2017-118585

(51) Int. Cl.
*C12Q 1/6851* (2018.01)
*B01L 3/00* (2006.01)
*B01L 7/00* (2006.01)

(52) U.S. Cl.
CPC .......... *C12Q 1/6851* (2013.01); *B01L 3/5027* (2013.01); *B01L 3/502715* (2013.01); *B01L 7/00* (2013.01); *B01L 2200/147* (2013.01); *B01L 2300/0636* (2013.01); *B01L 2300/0645* (2013.01); *B01L 2300/0816* (2013.01); *B01L 2300/0819* (2013.01); *B01L 2300/0883* (2013.01); *B01L 2300/18* (2013.01)

(58) Field of Classification Search
None
See application file for complete search history.

(56) References Cited

U.S. PATENT DOCUMENTS

| | | | |
|---|---|---|---|
| 2014/0220667 A1 | 7/2014 | Safavieh et al. | |
| 2017/0191122 A1* | 7/2017 | Hashimoto | C12Q 1/6823 |
| 2018/0127814 A1 | 5/2018 | Hashimoto et al. | |

FOREIGN PATENT DOCUMENTS

| | | | |
|---|---|---|---|
| CN | 104004652 A | 8/2014 | |
| JP | 4262336 | 5/2009 | |
| JP | 4397182 B2 | 1/2010 | |
| JP | 2014-505476 A | 3/2014 | |
| JP | 2018-68258 | 5/2018 | |
| JP | 2018-143197 A | 9/2018 | |
| WO | WO 2010/018465 | 2/2010 | |
| WO | WO 2013/158982 | 10/2013 | |
| WO | WO 2016/136033 | 9/2016 | |
| WO | WO-2016136033 A1 * | 9/2016 | C12Q 1/6823 |

OTHER PUBLICATIONS

Kivlehan, F. et al., Real-time electrochemical monitoring of isothermal helicase-dependent amplification of nucleic acids, Analyst, vol. 136, pp. 3635-3642 (Year: 2011).*

Safavieh, M. et at., High-throughput real-time electrochemical monitoring of LAMP for pathogenic bacteria detection, Biosensors and Bioelectronics, vol. 58, pp. 101-106 (Year: 2014).

Luo, J. et al., A real-time microfluidic multiplex electrochemical loop-mediated isothermal amplification chip for differentiating bacteria, Biosensors and Bioelectronics, vol. 60, pp. 84-91 (Year: 2014).

Ahmed, M.U. et al., Real-time electrochemical detection of pathogen DNA using electrostatic interaction of a redox probe, Analyst, vol. 138, pp. 907-915 (Year: 2013).

Stratagene Catalog, p. 38 (Year: 1988).

Minhaz Uddin Ahmed, et al., "Real-time electrochemical detection of pathogen DNA using electrostatic Interaction of a redox probe", Analyst, vol. 138, No. 3, Nov. 2012, pp. 10.

Bo Yao, et al., "Sensitive detection of microRNA by chronocoulometry and rolling circle amplification on a gold electrode", Chemical Communications, vol. 50, No. 68, Jul. 2014, pp. 3.

* cited by examiner

*Primary Examiner* — Teresa E Strzelecka
(74) *Attorney, Agent, or Firm* — Oblon, McClelland, Maier & Neustadt, L.L.P.

(57) ABSTRACT

According to one embodiment, a method of quantifying a target nucleic acid containing a first sequence in a sample is provided. The method includes preparing a substrate on which a plurality of detection regions are arranged, forming a reaction field by placing, on the substrate, a reaction liquid containing a sample, a primer set, and an amplification enzyme, maintaining the reaction field in an isothermal amplification condition, detecting a detection signal for each of the detection regions, determining, for each of the plurality of detection regions, whether positive or negative and detecting or quantifying the target nucleic acid based on the number of positive and/or a rise time of each of the positive detection signal.

4 Claims, 10 Drawing Sheets

Specification includes a Sequence Listing.

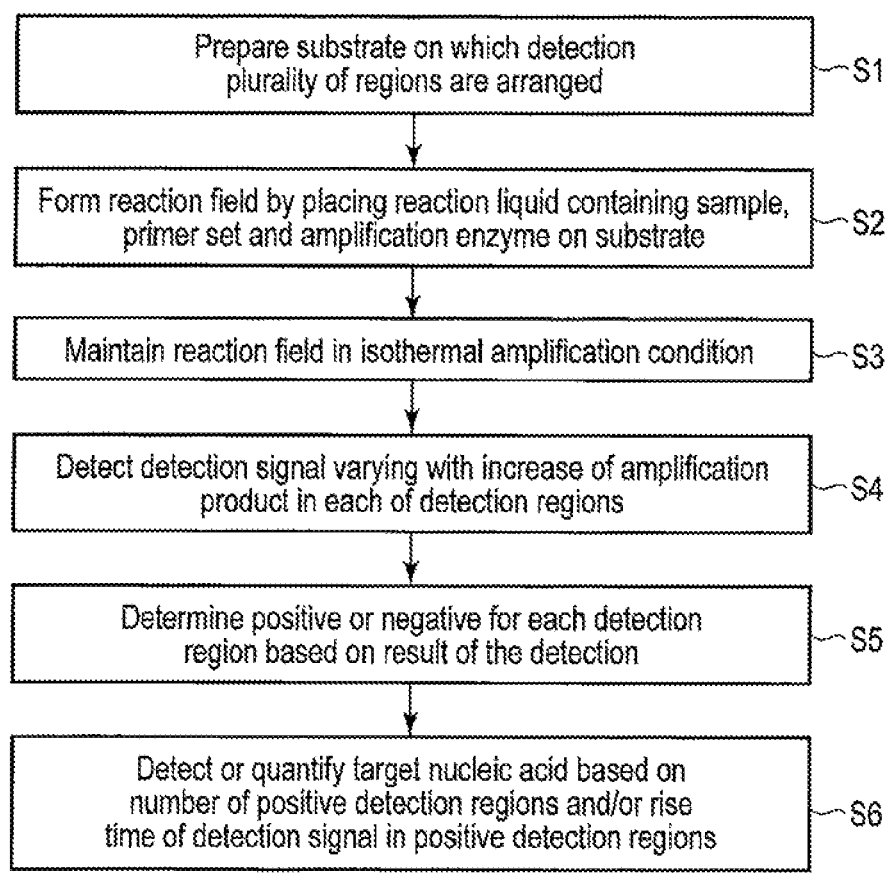
F I G. 1

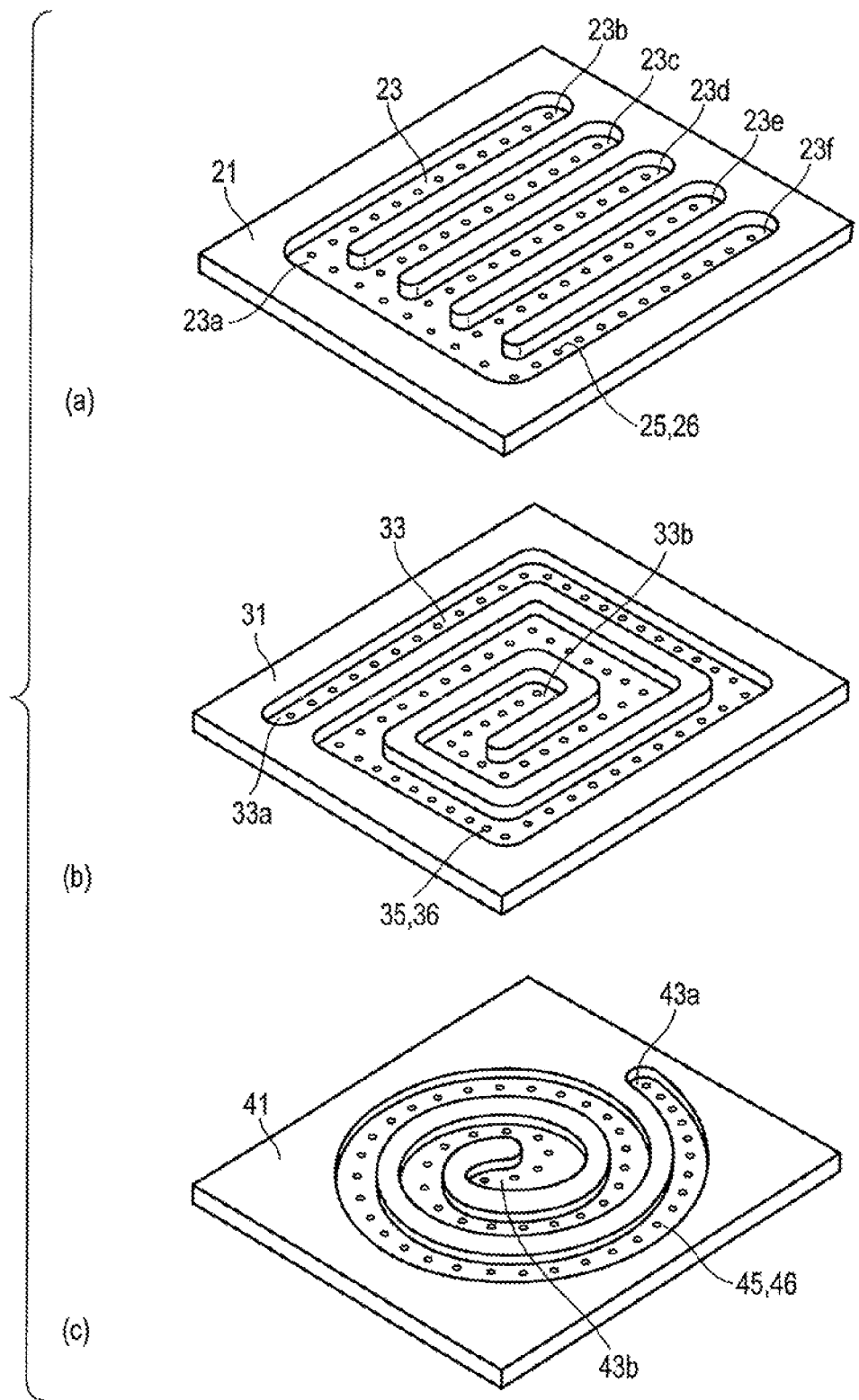
F I G. 3

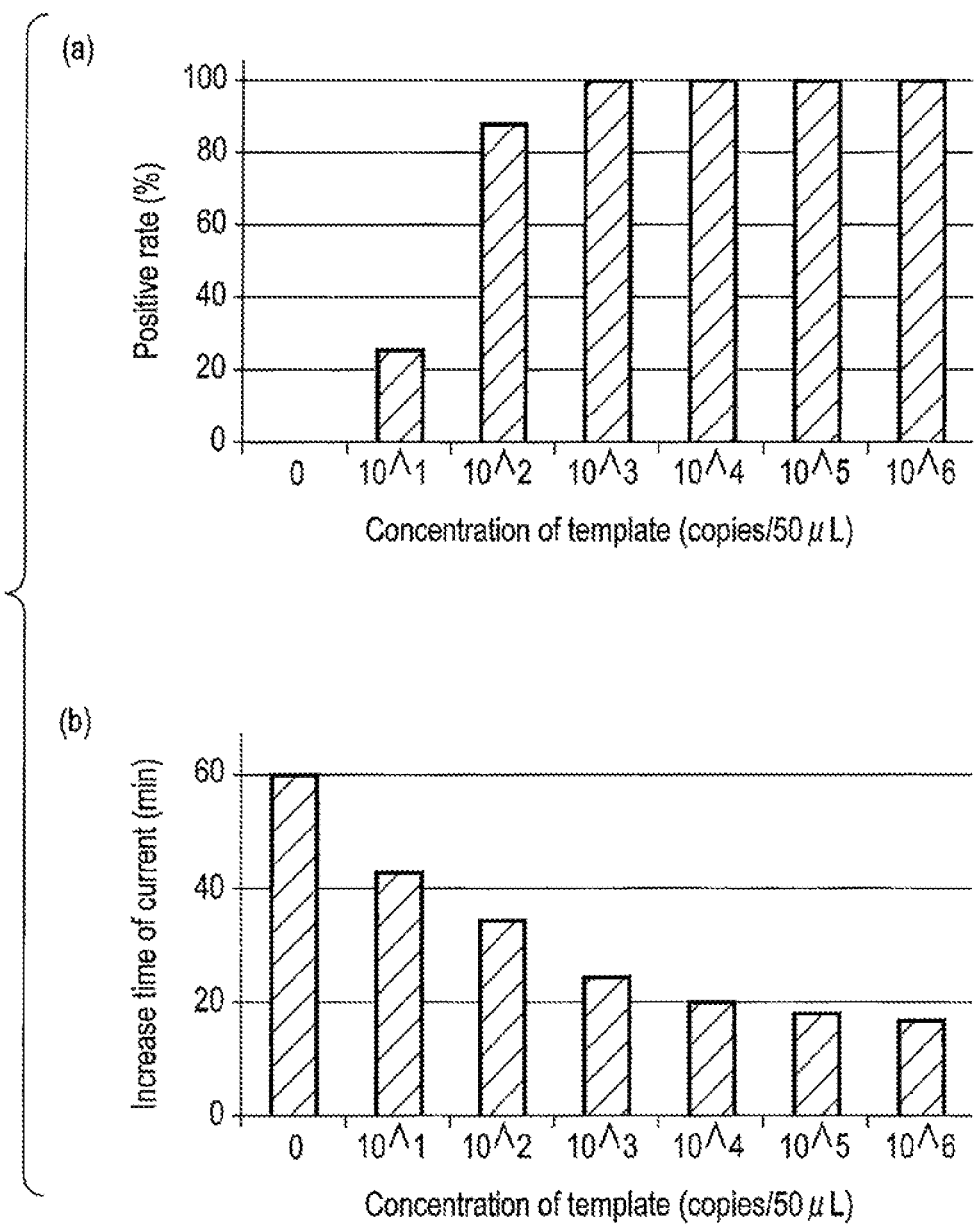
F I G. 11

SEQUENCE LISTING

<160> NUMBER OF SEQ ID NOS: 6

<210> SEQ ID NO 1
<211> LENGTH: 1000
<212> TYPE: DNA
<213> ORGANISM: Parvo virus

<400> SEQUENCE: 1

```
aaacgctaat acgactcact atagggcgat ctacgggtac tttcaataat cagacggaat      60
ttaaattttt ggaaaacgga tgggtggaaa tcacagcaaa ctcaagcaga cttgtacatt     120
taaatatgcc agaaagtgaa aattatagaa gagtggttgt aaataatttg gataaaactg     180
cagttaacgg aaacatggct ttagatgata ctcatgcaca aattgtaaca ccttggtcat     240
tggttgatgc aaatgcttgg ggagtttggt ttaatccagg agattggcaa ctaattgtta     300
atactatgag tgagttgcat ttagttagtt ttgaacaaga aatttttaat gttgttttaa     360
agactgtttc agaatctgct actcagccac caactaaagt ttataataat gatttaactg     420
catcattgat ggttgcatta gatagtaata atactatgcc atttactcca gcagctatga     480
gatctgagac attgggtttt tatccatgga aaccaaccat accaactcca tggagatatt     540
attttcaatg ggatagaaca ttaataccat ctcatactgg aactagtggc acaccaacaa     600
atatatacca tggtacagat ccagatgatg ttcaattta tactattgaa aattctgtgc     660
cagtacactt actaagaaca ggtgatgaat ttgctacagg aacatttttt tttgattgta     720
aaccatgtag actaacacat acatggcaaa caaatagagc attgggctta ccaccatttc     780
taaattcttt gcctcaagct gaaggaggta ctaactttgg ttatatagga gttcaacaag     840
ataaaagacg tggtgtaact caaatgggaa atacaaacta tattactgaa gctactatta     900
tgagaccagc tgaggttggt tatagtgcac catattattc ttttgaggcg tctacacaag     960
ggccatttaa aacaccttc cctttagtga gggttaataa                            1000
```

<210> SEQ ID NO 2
<211> LENGTH: 27
<212> TYPE: DNA
<213> ORGANISM: Artificial Sequence
<220> FEATURE:
<223> OTHER INFORMATION: synthetic primer

<400> SEQUENCE: 2

```
gagatattat tttcaatggg atagaac                                              27

<210> SEQ ID NO 3
<211> LENGTH: 23
<212> TYPE: DNA
<213> ORGANISM: Artificial Sequence
<220> FEATURE:
<223> OTHER INFORMATION: synthetic primer

<400> SEQUENCE: 3
caatgctcta tttgtttgcc atg                                                  23

<210> SEQ ID NO 4
<211> LENGTH: 48
<212> TYPE: DNA
<213> ORGANISM: Artificial Sequence
<220> FEATURE:
<223> OTHER INFORMATION: synthetic primer

<400> SEQUENCE: 4
gaacatcatc tggatctgta ccaaccatct catactggaa ctagtggc                       48

<210> SEQ ID NO 5
<211> LENGTH: 48
<212> TYPE: DNA
<213> ORGANISM: Artificial Sequence
<220> FEATURE:
<223> OTHER INFORMATION: synthetic primer

<400> SEQUENCE: 5
ctgtgccagt acacttacta agagtgttag tctacatggt ttacaatc                       48

<210> SEQ ID NO 6
<211> LENGTH: 23
<212> TYPE: DNA
<213> ORGANISM: Artificial Sequence
<220> FEATURE:
<223> OTHER INFORMATION: synthetic primer

<400> SEQUENCE: 6
acaggtgatg aatttgctac agg                                                  23
```

NUCLEIC ACID DETECTION OR QUANTIFICATION METHOD, CHIP AND ASSAY KIT THEREFOR, DEVICE FOR DETECTING OR QUANTIFYING NUCLEIC ACID AND PROGRAM THEREFOR

CROSS-REFERENCE TO RELATED APPLICATIONS

This application is a divisional application of U.S. application Ser. No. 15/907,700 filed Feb. 28, 2018, which is allowed and based upon and claims the benefit of priority from Japanese Patent Application No. 2017-118585, filed Jun. 16, 2017, the entire contents of which are incorporated herein by reference.

FIELD

Embodiments described herein relate generally to a nucleic acid detection or quantification method, a chip and an assay kit therefor, a device for detecting or quantifying nucleic acid and a program therefore.

BACKGROUND

At present, with progress of genetic-testing technology, the nucleic acid testing is carried out in various scenes such as clinical diagnosis and criminal investigations. The target genes are detected or quantified by, for example, the real-time PCR method or LAMP method. The real-time PCR method is accompanied by the amplification of nucleic acid, and therefore its sensitivity is high and the quantitative range is wide. The LAMP method can quantify or detect target genes without labeling the amplification product with a fluorochrome or the like. However, the quantifications or detections by these methods entail low accuracy in analysis.

As a technology with higher accuracy in quantification or detection, the digital PCR method has been introduced in practice. However, the digital PCR method requires to adjusting the concentration of the reaction liquid appropriately and dispensing the liquid into a great number of containers at an equal amount, which problematically involve complicated operations.

Under such circumstances, there is a demand for further development of a quantification or detection method which can detect nucleic acid simply at high sensitivity.

BRIEF DESCRIPTION OF THE DRAWINGS

FIG. 1 is a flowchart showing an example of a nucleic acid detection or quantification method in an embodiment.

FIG. 3 is a diagram showing an example of a substrate of the embodiment.

FIG. 6 is a block diagram showing an example of a device for detecting or quantifying nucleic acid of the embodiment.

FIG. 11 is a graph showing experimental results in Example 2.

DETAILED DESCRIPTION

Figure 2:
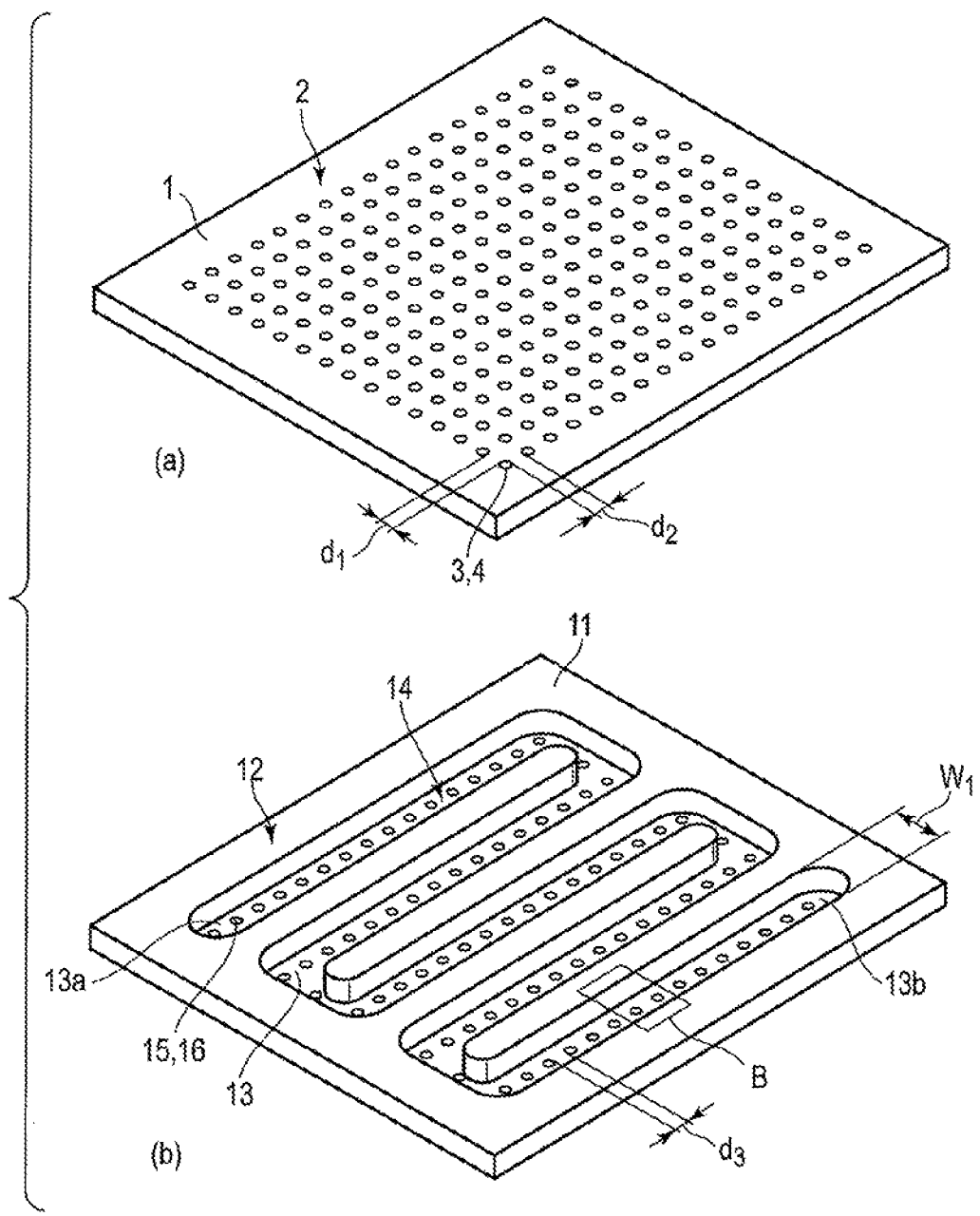
FIG. 2 is a diagram showing an example of a substrate of the embodiment.

In general, according to one embodiment, a nucleic acid detection or quantification method is a method of quantifying a target nucleic acid containing a first sequence in a sample. The method comprises preparing a substrate on which a plurality of detection regions are arranged; forming one reaction field by placing, on the substrate, a reaction liquid containing a sample, a primer set for isothermally amplifying the first sequence to obtain an amplification product, and an amplification enzyme; maintaining the reaction field in an isothermal amplification condition; detecting a detection signal varying with an increase of the amplification product in each of the plurality of detection regions; determining, for each of the plurality of detection regions, whether an amplification product exists in a vicinity (positive) or an amplification product does not exist (negative) based on the result of the detecting; and detecting or quantifying the target nucleic acid based on the number of positive detection regions and/or a rise time of the detection signal in each of the positive detection regions.

Various embodiments will be described below with reference to the accompanying drawings. Each figure is an exemplary diagram of an embodiment to aid understanding of the embodiment. The shapes, dimensions or ratios in the drawings may differ from those of the actual device, and may be appropriately changed in light of the subsequent explanation and the known art.

FIG. 1 shows a brief flow of an example of the nucleic acid detection or quantification method according to an embodiment.

The nucleic acid detection or quantification method is a method of quantifying a target nucleic acid containing the first sequence in a sample. The method comprises: (S1) preparing a substrate on which a plurality of detection regions are arranged; (S2) forming one reaction field by placing, on the substrate, a reaction liquid containing a sample, a primer set for isothermally amplifying the first sequence to obtain an amplification product, and an amplification enzyme; (S3) maintaining the reaction field in an isothermal amplification condition; (S4) detecting a detection signal varying with an increase of the amplification product in each of the plurality of detection regions; (S5) determining, for each of the plurality of detection regions, whether an amplification product exists in a vicinity (positive) or an amplification product does not exist (negative) based on the result of the detecting; and (S6) detecting or quantifying a target nucleic acid based on the number of positive detection regions and/or the rise time of the detection signal in each of the positive detection regions.

Each processing step will be described in detail below.

In step (S1), a substrate on which a plurality of detection regions is arranged is prepared.

The substrate is a solid phase which supports one reaction field to be formed in step (S2) described later. As the substrate, for example, metal, resin, glass, silicon or the like can be used. The shape of the substrate as a whole may be, for example, plate-like, container shape, or a part of each of these.

An example of the substrate is shown in FIG. 2, part (a). In one surface 2 of the substrate 1, a plurality of detection regions 3 are disposed. The detection regions 3 are those for detecting the detection signal from the reaction field formed on the one surface 2 of the substrate 1 in step (S2) described later.

As a material of the detection regions 3, metal, resin, glass, silicon or the like can be used. The material of the detection regions 3 is selected according to the material of the substrate, the type of the detection signal detected in step (S4), which will be described later.

The detection regions 3 are arranged in, for example, a regular array. Or the arrangement of the detection regions 3 may be random disposition at a uniform density. It is preferable that the detection regions 3 be arranged uniformly on all over the region adjacent to the reaction field on the surface 2 of the substrate 1, formed in the step (S2), which will be described later. With such a configuration, target nucleic acids are detected or quantified more accurately.

When the detection regions 3 are arranged in a regular array, it is preferable that intervals between adjacent pairs of detection regions, for example, arranged along a row direction and a column direction be substantially equal to each other.

The size of each detection region 3 should just be set depending on the predetermined size of the substrate 1 and the predetermined number of the detection regions 3, but, for example, the length is 0.001 to 10 mm and the width is 0.001 to 10 mm.

The shape of each the detection regions 3 should just be selected according to the type of signal so as to be able to detect a predetermined signal to be detected, and, for example, it is circular, quadrangular or polygonal. The number of the detection regions 3 arranged on a single substrate 1 should preferably be, for example, two or more. Ten or more is preferable because in which case, the accuracy in detection and quantification further improves.

Further, it is preferable that the detection regions 3 be the same as an identical to each other in area and shape. In particular, if the detection regions vary from each other in area, the accuracy in quantification degrades. Therefore, the dispersion in area should preferably be no more than 10%, or more preferably no more than 5%.

The detection regions 3 are arranged at an interval d1 along the row direction and an interval d2 along the column direction. That is, the intervals d1 and d2 are distances between two adjacent detection regions arranged along the row direction and the column direction, respectively. In other words, they are each the closest distance between two detection regions 3 adjacent to each other from an end of one detection region 3 to a corresponding end of the other detection region 3. The intervals d1 and d2 should preferably be no less than 0.1 mm. The intervals d1 and d2 should more preferably be no less than 0.5 mm, and even more preferably no less than 1 mm.

When the intervals d1 and d2 are 0.1 mm or more, such a phenomenon that a detection signal to be detected in a specific detection region is detected also in a different detection region arranged near can be suppressed, and the accuracy in quantification can be improved. If no less than 0.5 mm, the phenomenon is further suppressed, thereby further improving the accuracy in quantification. Especially, when 1 mm or more, even under such conditions that the target nucleic acid is short in length and the reaction time is long condition, the phenomenon that a detection signal to be detected in a specific detection region is detected also in a different detection region arranged near can be prevented, thereby further enhancing the accuracy in detection and quantification.

Here, the intervals d1 and d2 should preferably be no more than 10 mm. If the interval is excessively wide, the number of detection regions formable on one substrate decreases. As a result, the accuracy in quantification degrades and a great quantity of sample is required to achieve a desired accuracy in quantification.

The substrate 1 may comprise sensors 4 corresponding respectively to the detection regions 3. The sensors 4, which will be described later in detail, are, for example, electrodes, electrochemical sensors, optical sensors, or turbidity sensors. When the sensors 4 are provided, all of those corresponding respectively to the detection regions 3 on one substrate 1 should preferably be of the same kind.

The detection regions 3 may be each formed from a light-transmitting material. That is, the portions of the substrate 1, which correspond to the detection region 3, may be formed from a light-transmitting material. In that case, the detection signal can be detected from the detection regions with, for example, a sensor separated from the substrate 1.

In the substrate 1 with the above-described structure, one space is formed on the surface 2. That is, the space on the surface 2 is not divided for a plurality of detection regions 3. With this structure, when the reaction liquid is brought onto the surface 2 in step (S2), which will be described later, the reaction mixture is placed in such a state that it can flow to any location on the surface 2. As a result, one reaction field is formed. Therefore, in the substrate 1, it is possible to bring the reaction liquid onto all the detection regions 3 by one operation. Further, the volumes of the spaces on these respective detection regions 3 are constant.

Part (b) of FIG. 2 shows a further example of the substrate. In this example, a surface 12 of a substrate 11 comprises a flow channel 13 formed from a meandering groove. It is preferable that detection regions 15 be arranged by one or a plurality of rows along with the flow channel 13 in a bottom portion 14 of the flow channel 13. A width w1 of the flow channel 13 may be determined according to, for example, the size of the substrate 11, and preferably, for example, 0.01 to 50 mm. A depth of the flow channel should preferably be, for example, 0.01 to 10 m. The size of each detection region 15 may be selected depending on the size of a desired substrate 11, the number of desired detection regions 15, the width of the flow channel 13, or the like, but, for example, the length is 0.001 to 10 mm, and the width is 0.001 to 10 mm, etc.

The distance of two detection regions 15 adjacent to each other, that is, a closest interval d3 between the two regions from an end of one detection region 15 to an end of the other detection region 15 should preferably be no less than 0.1 mm, or more preferably no less than 0.5 ma or more, or even more preferably no less than 1 mm.

If the interval d3 is no less than 0.1 mm, such a phenomenon that a detection signal to be detected in a specific detection region is detected also in a different detection region arranged near does not easily occur, and the accuracy in quantification can be improved. If not less than 5 mm, the phenomenon is further suppressed and the accuracy in quantification further improves. Especially, if no more than 1 mm, even under conditions that the length of target nucleic acid is short and the reaction time is long, the phenomenon that a detection signal to be detected in a specific detection region is detected also in a different detection region arranged near can be prevented; therefore the accuracy in detection and quantification is further enhanced.

The number of detection regions 15 arranged in one substrate 11 should preferably be, for example, two or more. Ten or more is more preferably, the accuracy in detection is further enhanced.

The shape of the flow channel 13 may be one meandering groove such as that shown in part (b) of FIG. 2, or may be some other shape. For example, it may be a comb-like shape as the flow channel 23 shown in part (a) of FIG. 3, or a square spiral shape as the flow channel 33 shown in part (b) of FIG. 3, or a circular spiral shape as the flow channel 43 shown in part (c) of FIG. 3.

The corners of the flow channels 13, 23 and 33 should preferably be chamfered. With the chamfered corners, it is possible to suppress the production of bubbles while bringing the reaction liquid into the flow channel in step (S2), which will be described later, which may cause blocking of the amplification reaction.

The substrates 11, 21, 31 and 41 may respectively comprise sensors 16, 26, 36 and 46 similar to the above-described sensor 4, in the detection regions 15, 25, 35 and 45. Or, the detection regions 15, 25, 35 or 45 may be formed from a light-transmitting member as described above.

Next, in step (S2), the reaction liquid is placed an the surface of the substrate, where a plurality of detection regions exists, so as to form a reaction field. A "reaction field" is a region where an amplification reaction occurs, and the region is defined by the reaction liquid. In other words, a reaction field is a region where a reaction liquid exists.

The reaction liquid contains a sample, a primer set and an amplification enzyme.

The sample is a substance to be examined as to the presence/absence or quantity of a target nucleic acid. In other words, a sample is an object to be analyzed in the nucleic acid detection or quantification method of the embodiment. For example, the sample may be bio-materials containing blood, serum, leukocyte, urine, feces, sweat, saliva, oral mucosa, expectoration, lymph, spinal fluid, lacrimal fluid, mother milk, amniotic fluid, semen, tissue, biopsy and culture cells, environmental materials collected from the environment, artificial nucleic acids or the like, or mixtures of those. Further, a preparation formulated using any of above materials may as well be used as the sample. For example, a pretreatment my be carried out on any of above materials to be used as a sample in the embodiment. The pretreatment may be any conventional means known by itself, such as a fragment, homogenization or extraction, for example. For example, any of above materials may be collected from an organism or environment, and formulated into a condition suitable for the nucleic acid detection. For example, a liquid containing a nucleic acid component which is obtained by extracting a nucleic acid from any of the above materials by any means can be used as the sample.

Target nucleic acid is nucleic acid which should be detected or quantified in the nucleic acid detection or quantification method of the embodiment. The target nucleic acid includes the first sequence. The first sequence is a sequence used as the index of the existence of the target nucleic acid, and a sequence to be amplified in the nucleic acid detection or quantification method of the embodiment so as to detect or quantify the target nucleic acid. The first sequence is a sequence selected from the sequence covering the full length of the target nucleic acid, and should preferably be, for example, a sequence specific to the target nucleic acid. The target nucleic acid is a single strand nucleic acid. The state of the target nucleic acid in the sample may be a single strand or a double strand formed from a target nucleic acid and a nucleic acid chain complementary to the target nucleic acid. The length of the target sequence may be, for example, 50 to 500 bases, and preferably, 100 to 300 bases.

The length of the first sequence may be, for example, 3 to 10 bases, 10 to 20 bases, 20 to 30 bases, 30 to 40 bases, 40 to 50 bases and 50 to 60 bases, 60 to 70 bases, 70 to 80 bases, 80 to 90 bases or 90 to 100 bases, and preferably, 10 to 50 bases.

The primer set is that for isothermal amplification for amplifying the above-described first sequence to obtain an amplification product. Based on the kind of the amplification method used for the nucleic acid detection or quantification method, the sequence of each primer contained in the primer set should just be designed and/or selected so as to amplify the first sequence. The amplification method used for the nucleic acid detection or quantification method is an isothermal amplification method. The employable amplification method may be, for example, LAMP, RT-LAMP, SDA, NASBA, RCA, LCR, TMA, SmartAmp (registered trademark) or ICAN (registered trademark). For example, the primer set contains a first primer complementary to one terminal of the first sequence and a second primer homologous to the other terminal of the first sequence. With these primers, a range to be amplified on the target nucleic acid is specified.

In the case where the primer set is that for LAMP, one primer set may contain an PIP primer as the first primer and a BIP primer as the second primer. The primer set for LAMP may further contain an F3 primer, B3 primer and LP primer, that is, LF primers and/or LB primers.

For example, when the target nucleic acid in a sample is a single-stranded DNA, a complementary strand is formed by the primer set, and further the amplification reaction advances using it as a template. Moreover, when the target nucleic acid is RNA, a reverse transcription reaction is carried out and the reverse transcription product is subjected to the amplification reaction.

The amplification enzyme may be selected based on the kind of each of the target nucleic acid, the isothermal amplification method employed and the primer set, and the presence/absence of a reverse transcription reaction, etc. The amplification enzyme may be DNA-polymerase, RNA-polymerase, or the like for example. The DNA polymerase should preferably be, for example, Bst, Bst2.0, Bst3.0, GspSSD, GspM, Tin, Bsm, Csa, 96-7, phi29, Omini-Amp (registered trademark), Aac, BcaBEST (registered trademark), Displace Ace (registered trademark), SD, Strand Displace (registered trademark), TOPOTAQ, Isotherm2G, Taq or a combination of any of these. Use of Bst, GspSSD or Tin is more preferable because they enhance the sensitivity in the detection and quantification. In addition to the amplification enzyme, any reverse transcriptase may be further employed.

The reaction liquid may further contain magnesium in addition to the above-described ingredients. The concentration of magnesium in the reaction liquid should just be selected based on the kind of the detection signal, but should be, for example, no more than 30 mM, and more preferably, 4 mM to 10 mM. With this concentration, the amplification reaction is promoted and also various sequences of a wide range, which do not depend on the sequence, can be amplified efficiently. Thus, various types of sequences can be detected efficiently.

The reaction liquid may contain some other ingredients required for the amplification reaction in addition to the above-described ingredients. Such ingredients may be, for example, a marker substance which producing a signal according to an increase in amplification produce, a salt, a substrate such as deoxynucleoside triphosphoric acid (dNTP), which is required to form a new polynucleotide chain whose origin of replication is the primer, a thickener as a reaction reagent, a buffer for pH adjustment, a surfactant, ion for enhancing the annealing specificity and/or ion which gives rise to a cofactor of the amplification enzyme, etc. When performing a reverse transcription simultaneously, the reaction liquid may further contain a reverse transcriptase and a substrate required therefor, and the like.

The marker substance is a substance producing the detection signal which changes with the increase in an amplification product. For example, the marker substance is a substance which increases or decreases the production of detection signals when an amplification product exists as compared with the case where the amplification product does not exist. Or, for example, it is a substance which increases or decreases the quantity of the detection signal produced from there according to the amount of the amplification product presence. For example, the marker substance is a substance producing an electric signal or an optical signal, or the like, as will be described later in detail. The reaction liquid may not necessarily contain a marker substance. In that case, the signal correlated to the turbidity of the reaction liquid may be used as the detection signal to quantify or detect the target nucleic acid.

The salt may be any of well-known salt used, for example, to maintain an appropriate amplification environment in the nucleic acid amplification reaction. Maintaining an appropriate amplification environment in the nucleic acid amplification reaction means that, for example, the amplification enzyme maintains its tertiary structure so as to optimize the nucleic acid amplification activity. The salt is potassium chloride, for example. The concentration of the salt in the reaction liquid should preferably be, for example, 5 to 300 mol/L.

The reaction liquid described above is placed on the surface of the substrate, where the detection regions are present, to form one reaction field. The one reaction field is a reaction field formed in one continuous region. For example, one reaction field is formed by bringing a reaction liquid on the surface of any of the above-described substrates, where the detection regions are present.

For example, when using the substrate 1 illustrated in part (a) of FIG. 2, a reaction field is formed by bringing the reaction liquid on the surface 2 of the substrate 1. When using the substrate of illustrated in part (b) of FIG. 2, a reaction field is formed by bringing the reaction liquid into the flow channel 13. In order to bring the reaction liquid to the flow channel 13, for example, the reaction liquid is injected from a liquid inlet 13a, and the air in the flow channel 13 is extracted from a discharge liquid outlet 13b. When using the substrate illustrated in part (b) of FIG. 3, the reaction liquid can be brought into the flow channel 23 by, for example, injecting the reaction liquid from a liquid inlet 23a and extracting the air from the discharge liquid outlets 23b to 23f. When using the substrate illustrated in part (b) of FIG. 3, the reaction liquid can be brought into the flow channel 33 by, for example, injecting the reaction liquid from a liquid inlet 33a and extracting the air from the discharge liquid outlet 33b. When using the substrate illustrated in part (c) of FIG. 3, the reaction liquid can be brought into the flow channel 43 by, for example, injecting the reaction liquid from a liquid inlet 43a and extracting the air from the liquid discharge outlet 43b.

The ingredients of the reaction liquid should just be each contained in the reaction liquid which forms the reaction field. Therefore, for example, the ingredients of the reaction liquid may be each contained in the reaction liquid before the reaction liquid is brought onto the substrate. Alternatively, the ingredients of the reaction liquid may be prepared separately from each other and may be brought into the reaction liquid at the same time as, before or after the reaction liquid is brought onto the substrate. Or before the reaction liquid is brought onto the substrate, some of the ingredients may be releasably immobilized to a solid phase or the like, which is a surface in contact with the reaction field, and brought into the reaction liquid by being released into the reaction liquid when the reaction liquid is brought thereto.

In step (S3), the reaction filed is maintained in an isothermal amplification condition.

The isothermal amplification condition is selected based on, for example, the kind of the isothermal amplification method employed, the kind of the primer set, the kind of the target nucleic acid, and/or the kind of the amplification enzyme, etc. Maintaining the isothermal amplification reaction condition is, for example, maintaining the temperature of the reaction field at 25° C. to 70° C. It is more preferable to maintain the temperature at 55° C. to 65° C. The isothermal amplification reaction condition should preferably be a LAMP amplification reaction condition. When target nucleic acid exists in a sample, the amplification reaction occurs by maintaining the reaction field under an isothermal amplification reaction condition, and the first sequence thereof is amplified, and an amplification product is produced.

The amplification product is produced in the position where the target nucleic acid exists on the surface of the substrate, where the detection region is disposed, and it increases and remains in its vicinity. For example, the amplification product amplified from one target nucleic acid molecule remains in a range of 0.001 to 1 mm from the position where the target nucleic acid initially existed. On the contrary, the amplification product hardly exists in the positions other than where the target nucleic acid exists or its vicinity on the surface.

In step (S4), the detection signal is detected in each of the detection regions.

The detection signal is a signal to be detected, which varies with the increase in the amplification product. Such a signal is, for example, an electric signal or optical signal produced from the marker substance which exists in the reaction field or a signal correlated to the turbidity of the reaction liquid, as will be described later in detail.

The detection signal is detected in a detection region. The detection signal may be detected by the above-described sensor provided in the detection region. Or the detection signal may be detected from a detection region by a sensor or the like, separated from the substrate. The detection signal is detected in all the detection regions arranged on the substrate.

The detection is performed at, for example, the end point of the amplification reaction, or may be performed sequentially. The sequential detection may be continuous, or intermittent, in which the detection is carried out a plurality of times at a predetermined time interval. For example, the continuous detection may be monitoring of the detection signal. It may detect the rise time of the detection signal.

In step (S5) it is determined whether an amplification product exists (positive) or does not exist (negative) in the vicinity of each of the detection regions.

When the detection of step (S4) is performed in the end point of an amplification reaction, the detection signal from a detection region disposed in the position on the substrate, where the amplification product is produced and increased increases or decreases as compared to the detection signal before the amplification reaction, or the detection signal from a detection region where the target nucleic acid does not exists therearound. Therefore, a detection region where the detection signal increases or decreases as compared to that before the amplification or other detection region can be determined as that "an amplification product exists in its vicinity (positive)". On the other hand, a detection region which is not so can determined as that "an amplification product does not exist in its vicinity (negative)".

Figure 4:
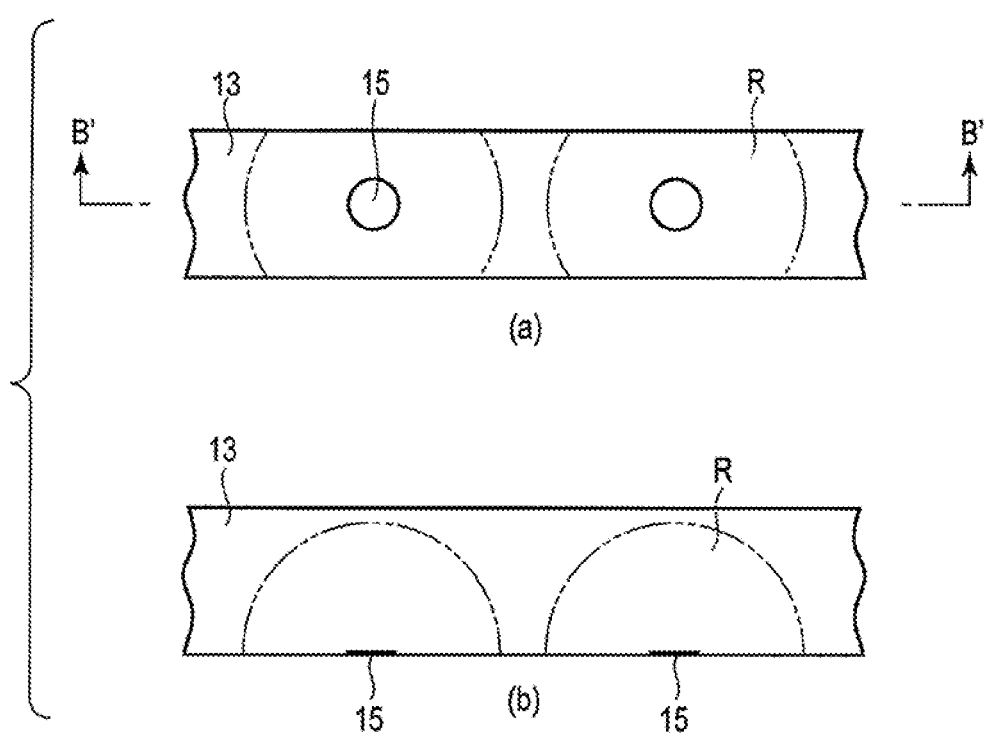
FIG. 4 is an enlarged schematic diagram showing a flow channel of a substrate of the embodiment.

The term "vicinity" is defined as within a range where the existence of an amplification product can detected with a detection means employed, such as a sensor. An example of the range in which the existence of an amplification product can be detected is shown in parts (a) and (b) of FIG. 4. Part (a) of FIG. 4 is an enlarged plan view of a portion B encircled in part (b) of FIG. 2. Part (b) of FIG. 4 is a cross section taken along line B'-B' in part (a) of FIG. 4, part (a). A range R in which the existence of an amplification product can be detected is a region in the reaction field in the flow channel 13. The region is that defined as the distance from an edge of a detection region 15 is specified by a value, and is approximately hemispherical. The distance varies depending on the detection means, but it is, for example, 0 to 10 mm.

Based on the determination made above, the number of positive detection regions and the number of negative detection regions in one reaction field can be obtained.

When the detection of step (S4) is carried out with time, the detection signal is produced from a detection region on the substrate, located in a position where the amplification product is produced and increased. This detection signal has a rise time, that is, the time required for the size of the detection signal to exceed a predetermined threshold, shorter as compared to that of the detection signal from a detection region around where a target nucleic acid does not exist. Therefore, a detection region where the rise of an increase of a detection signal is observed in a shorter time as compared to other detection regions is determined as that "an amplification product exists in its vicinity (positive)" and a detection region which is not so is determined as that "an amplification product does not exist in the vicinity (negative)". Based on this, the number of positive detection regions and the number of negative detection regions in one reaction field can be determined.

In step (S6), the target nucleic acid is detected or quantified from the number of positive detection regions obtained in step (S5) and/or the rise time of the detection signal in each of the positive detection regions.

For example, when the number of positive detection regions is 0, it is determined that any target nucleic acid does not exist in the sample.

When both positive and negative detection regions exist, the quantity of the target nucleic acid present in the sample can be calculated from the number of positive detection regions. The calculation may be based on, for example, a statistical procedure. As the statistical procedure, a most probable number (MN) method can be used.

The most probable number method is a procedure of acquiring the maximum likelihood estimated value (most probable number: MPN) of the quantity of a target nucleic acid in a sample by the following formula 1.

$$\text{MPN} = (\Sigma_{gi})/(\Sigma_{tjmj}\Sigma(tj-gj)_{mj})^{1/2} \quad \text{Formula 1}$$

where:
$\Sigma_{gi}$ is a sum of the values of the positive detection regions;
$\Sigma_{tjmj}$ is a sum of values of (number of detection regions× dilution rate); and
$\Sigma(tj-gj)_{mj}$ is a sum of values of (number of negatives× dilution rate).

When the reaction liquid is not diluted, the most probable number (MPN) can be obtained by the following Formula 2.

$$\text{MPN} = 1/m \times 2.303 \times \log((\text{number of detection regions})/(\text{number of negatives})) \quad \text{Formula 2}$$

where m is a reaction volume per detection region.

The reaction volume per detection region can be obtained by calculating out m, which is obtained by, for example, applying to Formula 2, a standard sample nucleic acid of a known concentration is amplified on a substrate to be used, thus detecting detection signals, and the number of positives obtained by detecting the detection signals, the concentration of the standard sample nucleic acid and the number of detection regions on the substrate. With this method, it is possible to detect, for example, 1 to $10^4$ copies/mL of target nucleic acid contained in the sample.

Incidentally, when a great number of target nucleic acids exist in a sample, the target nucleic acids existing in the vicinity of every detection region may be detected as positive. Here, as the quantity of target nucleic acid existing in the sample is greater, the rise in the increase of the detection signal is observed in a shorter time in all the detection regions. In that case, the target nucleic acid can be detected or quantified by, for example, the following manner. A plurality of different standard sample nucleic acids whose quantities of nucleic acid present are already known are used to prepare a calibration curve of the rise time of the detection signal with respect to the quantity of nucleic acid present, and the calibration curve is compared with the measurement result of the rise time in the target nucleic acid. Thus, the quantity of the target nucleic acid present in a sample can be calculated. With this method, it is possible to detect, for example, $10^4$ to $10^9$ copies/mL of target nucleic acid contained in the sample.

With step (S6) described above, the target nucleic acid in a sample can be detected or quantified.

According to the nucleic acid detection or quantification method described above, there is no need to dilute a sample or divide the reaction liquid, but with such a simple process of forming one reaction field, that is, the reaction liquid is brought onto one continuous region on a substrate, the target nucleic acid can be detected at higher accuracy. For example, according to the method of the embodiment, it is possible to detect, for example, 1 to $10^9$ copies/L of target nucleic acid contained in the sample.

The above-described procedure can be realised because the amplification method is of the isothermal type. To explain, if an amplification method such as PC method carried out in temperature variation, are used, the convection of the reaction liquid occurs during the reaction, which eventually causes diffusion of the amplification product, and the amplification product may move even to the position of a detection region where the target nucleic acid does not initially exist. Therefore, the presence/absence and/or the quantity of the amplification product existing in the vicinity of a predetermined detection region can not be correctly detected. However, with the method of the embodiment, which adopts the isothermal amplification, the amplification product does not move but remains at the position where the target nucleic acid initially existed. In this manner, the detection region where the target nucleic acid exists can be identified accurately, and the quantity of the amplification product is accurately reflected in the detection signal. Therefore, it is possible to accurately quantify and detect the target nucleic acid.

For example, with a substrate comprising any of the flow channels described above, it becomes even harder for the reaction liquid to move, and therefore the target nucleic acid can be quantified or detected even more accurately.

Moreover, according to the nucleic acid detection or quantification method of the embodiment, the amplification reaction is carried out on a substrate comprising a plurality of detection regions located at predetermined positions, and the detection signals are obtained from all the detection regions. With this structure, regardless of what positions of the reaction field, the target nucleic acid exists, the information covering the entire reaction field can be obtained without bias. Therefore, it is possible to estimate more accurately the positions where the target nucleic acid exists. As a result, the target nucleic acid can be detected and quantified at higher accuracy. Here, for example, even in the case where the target nucleic acids of samples obtained from a plurality of objects are to be detected or quantified, if substrates of the same structure are used according to the nucleic acid detection or quantification method of the embodiment, the results can be obtained at the same accuracy regardless of the samples. Thus, even more highly reliable detection and quantification can be carried out. In the case where the results obtained are compared each other among the samples as well, an even more highly reliable comparison results can be obtained.

Examples of the nucleic acid detection or quantification method described above, in which an electric signal, an optical signal, and a signal correlated to turbidity are used, respectively, will be described in detail.

The Nucleic Acid Detection or Quantification Method Using Electric Signal.

Figure 5:
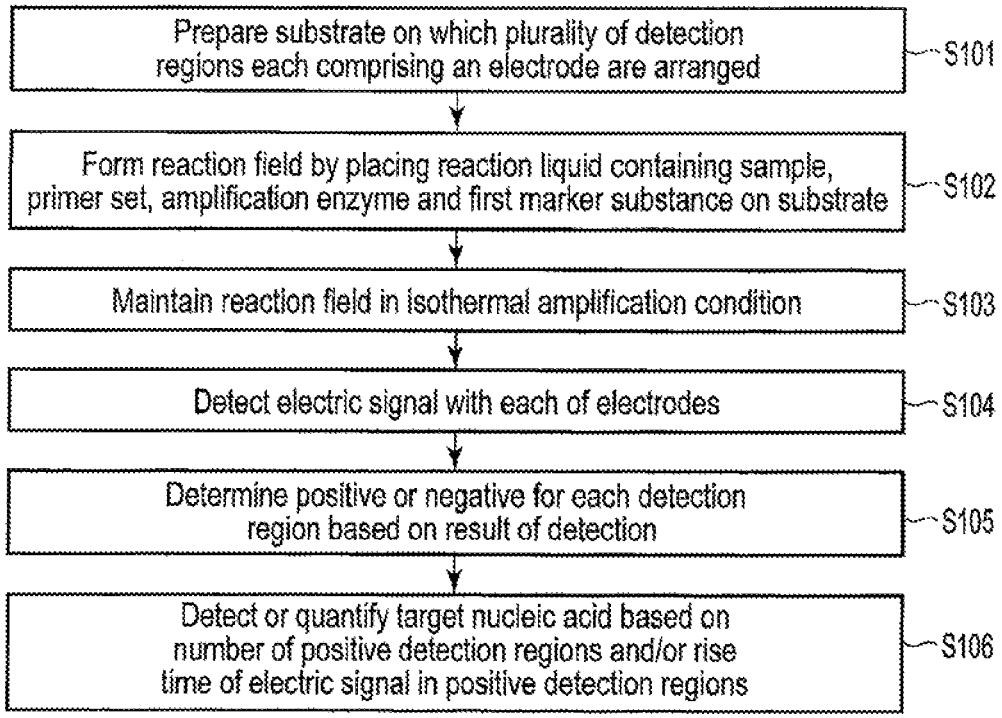
FIG. 5 is a flowchart showing an example of a nucleic acid detection or quantification method of the embodiment.

FIG. 5 shows a flowchart schematically illustrating the nucleic acid detection or quantification method using electric signal.

The nucleic acid detection or quantification method comprises: (S101) preparing a substrate on which a plurality of detection regions each comprising an electrode are arranged; (S102) forming one reaction field by placing, on the substrate, a reaction liquid containing a sample, a primer set for isothermally amplifying the first sequence to obtain an amplification product, an amplification enzyme and a first marker substance producing an electric signal varying with the increase of the amplification product; (S103) maintaining the reaction field in an isothermal amplification condition; (S104) detecting an electric signal with each of the electrodes; (S105) determining whether an amplification product exists in its vicinity (positive) or an amplification product does not exist in ins vicinity (negative) for each of a plurality of detection regions based on the result of the detection; and (S106) detecting or quantifying the target nucleic acid from the number of positive detection regions and/or the rise time of the electric signals in each of the positive detection regions.

In step (S101), a substrate on which a plurality of detection regions each comprising an electrode are arranged, is prepared.

As the substrate, for example, any one of those shown in FIGS. 2 and 3, which comprise electrodes corresponding to a plurality of detection regions, can be used. The electrodes can be obtained, for example, by forming metal patterns of a predetermined shape such as a dot on each of the detection regions on the substrate. The metal patterns can be formed, for example, by using a photolithographic method. Such a method is preferable because thereby more electrodes can be formed on the substrate. As the metal, for example, gold is preferable because of its high sensitivity.

It is preferable to form, for example, two or more detection regions, that is, electrodes, on one substrate. It is even more preferable to form ten or more, because in which case the accuracy is further improved.

The electrodes are each disposed so as to be able to detect the electric signal from the first marker substance existing on the reaction field. In other words, the electrodes are each arranged so as to be at least partially brought into contact with the reaction liquid when the reaction liquid is brought onto the substrate to form the reaction field.

The substrates each may further comprise a pad. The pad is electrically connected to a respective electrode, from which the data on the electric signal obtained with the electrode can be extracted. Further, the substrate may further comprise a reference electrode and a counter electrode.

In step (S102), the reaction liquid is placed on the surface of the substrate, where a plurality of detection regions exists, and thus a reaction field is formed.

The reaction liquid contains a sample, a primer set, an amplification enzyme and a first marker substance. The sample, primer set and amplification enzyme may be any one of those described above.

The first marker substance is a substance producing an electric signal upon the increase of the amplification product. For example, the first marker substance is, for example, an oxidizer whose oxidation-reduction potential can be an electric signal.

Examples of the first marker substance are ferricyanide ion, ferrocyanide ion, an iron complex ion, a ruthenium complex ion and a cobalt complex ion. These marker substances can be each obtained by dissolving potassium ferricyanide, potassium ferrocyanide, an iron complex, a ruthenium complex or a cobalt complex into a reaction liquid. The concentrations in those reaction liquids may be, for example, 10 µM to 100 mM, or about 1 mM.

For example, when ferricyanide ion ($Fe(CN)_6^{4-}$) is used as the first marker substance, electrons are emitted by the oxidation reaction of $Fe(CN)_6^{4-}$ into $Fe(CN)_6^{3-}$. These electrons repel the amplification product having negative charge and move away from the amplification product. Therefore, in an electrode around which an amplification product exists, the current (electric signal) detected decreases as the amplification product increases.

The first marker substance may be used in combination with another marker substance. When an electrochemically active substance having negative or positive charge and for example, a nucleic acid probe labeled with ferrocene are used in combination in a reaction field, ferrocene serves as a mediator to amplify the electric signal, and thus the sensitivity is further improved.

Or the first marker substance may be a redox probe. The redox probe is a substance which has an oxidation reduction potential of, for example, −0.5V to 0.5V, and it electrostatically binds to the amplification product in the reaction liquid. By applying voltage to the electrode, the redox probe bound to the amplification product is oxidized or reduced, and electrons are emitted by the reaction. Therefore, for example, in the electrode disposed in the position where the amplification product exists, the current (electric signal) detected increases as the amplification product increases, or the peak potential of the oxidation-reduction potential detected is shifted in a negative direction.

In the electrode around which an amplification product exists, whether the current (electric signal) detected increases as the amplification product increases or the peak potential of the oxidation-reduction potential detected is shifted in the negative direction can be adjusted, for example, by changing the magnesium concentration in the reaction liquid. For example, when the magnesium concentration is 4 mM to 30 mM, the current to be detected can increase as the amplification product increases. Or as the amplification product increases, the peak potential of the oxidation reduction potential to be detected can be shifted in the negative direction. Therefore, it is possible to carry out even a higher-accuracy measurement by further detecting the peak potential of the oxidation-reduction potential in addition to the electric signal.

The redox probe is a metal complex, for example. The metal complex to be used as the redox probe may contain, for example, ruthenium (Ru), rhodium (Rh), platinum (Pt), cobalt (Co), chromium (Cr), cadmium (Cd), nickel (Ni), zinc (Zn), copper (Cu), osmium (Os), iron (Fe), or silver (Ag) as a central metal. The metal complex may be, for example, amine complex, cyano complex, halogen complex, hydroxy complex, cyclopentadienyl complex, phenanthroline complex or bipyridine complex. Further, redox probes such as methylene blue, Nile blue and crystal violet, can also be used.

For example, the first marker substance is ruthenium hexaamine (RuHex). Here, when an amplification product exists, $RuHex^{3+}$ bound to the amplification product applies voltage to the electrode to be reduced to $RuHex^{2+}$, thereby emitting an electron. As the electron flows into the electrode, the amplification product can be detected.

The concentration of the redox probe in the reaction liquid is, for example, 0.1 μM to 100 mM, but preferably, 25 μM to 3 mM, and more preferably, 1 mM in which case, the detection sensitivity of the nucleic acid can be improved. If excessively less, it cannot sufficiently bind to the amplification product and the sensitivity may be undesirably degraded. On the other hand, if excessively high, the amplification reaction may be blocked. Especially when the first marker substance is ruthenium hexaamine (RuHex), it is preferable that RuHex be contained in the reaction liquid in a range of 25 μM to 3 mM.

The reaction mixture may contain magnesium at a desired concentration to be selected based on the kind of the first marker substance or the kind of detection signal or the like as described above.

The reaction mixture may contain a salt, a substrate such as deoxynucleoside triphosphoric acid (dNTP), which is required to form a new polynucleotide using the primer as an origin of replication, a thickener as a reaction reagent, a buffer for pH adjustment, a surfactant, ion for enhancing the annealing specificity and/or ion which gives rise to a cofactor of the amplification enzyme, etc. When carrying out reverse transcription simultaneously, the reaction liquid may contain reverse transcriptase and a desired ingredient required for the amplification reactions, such as a substrate required therefor.

The reaction liquid described above is placed on the surface of the substrate, where the detection regions are disposed, to form one reaction field. The reaction field can be formed by a method similar to any of those described above.

In step (S103), the reaction field is maintained in the isothermal amplification condition. This step can be carried out, for example, by a procedure similar to that of step (S3) described above.

In step (S104), the electric signal is detected with an electrode in a plurality of detection regions.

The electric signal is obtained from the first marker substance. The electric signal may be, for example, a current value, a potential value, a capacitance value, an impedance value or the like. The signal is detected by each electrode provided in the detection regions. For example, a plurality of kinds of electric signals such as a current value and a potential value may be measured. The detection may be carried out, for example, by a procedure similar to that described in step (S4) described above, for example, may be carried out at the end point of the reaction or sequentially during the reaction.

In step (S105), it is determined whether an amplification product exists (positive) or does not exist (negative) in the vicinity of each of the detection regions based on the result of the detection. This step can be carried out, for example, by a procedure similar to that of step (S5) described above. In this embodiment, the "vicinity" is defined, for example, as a region on the reaction field, located within such a distance from an edge of the electrode provided in the respective detection region is in a range of 0 to 10 mm.

In step (S106), the target nucleic acid is quantified from the number of positive detection regions, and/or the rise time of the electric signals. This step can be carried out, for example, by the same procedure as that of step (S6) described above.

According to the method described above, the target nucleic acid can be quantified simply at high sensitivity.

As an alternative embodiment which adopts the nucleic acid detection or quantification method using an electric signal, an electrochemical sensor may be employed in place of the electrode. Here, the electrochemical sensor should just be a well-known electrochemical sensor which can detect an electric signal from the above-described first marker substance.

The Nucleic Acid Detection or Quantification Method Using Optical Signal

Figure 6:
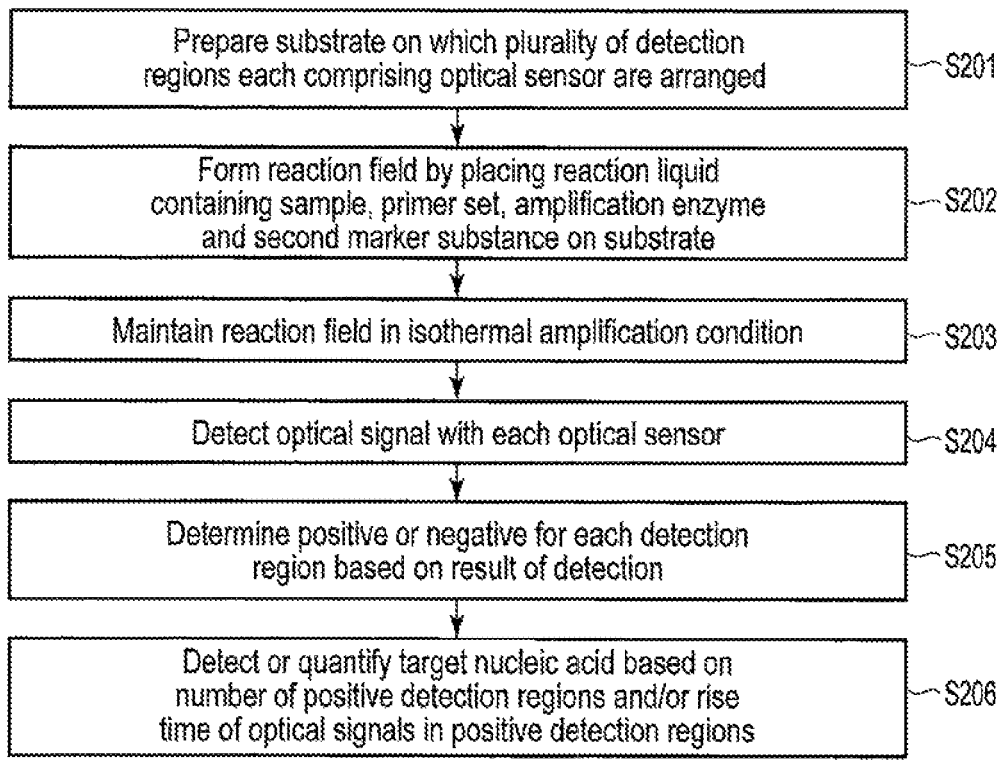
FIG. 6 is a flowchart showing an example of a nucleic acid detection or quantification method of the embodiment.

FIG. 6 is a flowchart schematically illustrating a nucleic acid detection or quantification method using an optical signal.

The nucleic acid detection or quantification method comprises: (S201) preparing a substrate on which a plurality of detection regions each comprising an optical sensor are arranged; (S202) forming one reaction field by placing, on the substrate, a reaction liquid containing a sample, a primer set for isothermally amplifying the first sequence to obtain an amplification product, an amplification enzyme and a second marker substance producing an optical signal varying with the increase of the amplification product; (S203) maintaining the reaction field in an isothermal amplification condition; (S204) detecting an optical signal with each of the optical sensors; (S205) determining whether an amplification product exists in its vicinity (positive) or an amplification product does not exist in ins vicinity (negative) for each of a plurality of detection regions based on the result of the detection; and (S206) detecting or quantifying the target nucleic acid from the number of positive detection regions and/or the rise time of the optical signals in each of the positive detection regions.

In step (S201), a substrate on which a plurality of detection regions each comprising an optical sensor are arranged, is prepared.

As the substrate, for example, any one of those shown in FIGS. 2 and 3, which comprise optical sensors corresponding to a plurality of detection regions, can be used. The optical sensors are each disposed so as to be able to detect the optical signal from the second marker substance existing on the reaction field. The optical sensor should just be any conventionally known sensor which can detect fluorescence, light emission or the like. For example, the optical sensor is an element or the like, which detect an optical signal such as fluorescence or luminescence and convert it into an electric signal.

Or as the substrate, for example, any of those shown in FIGS. 2 and 3, in which each of the detection regions is formed from a light-transmitting material can be employed. The light-transmitting material is, for example, resin. In this case, for example, signals can be detected by an optical sensor separated from the substrate. Or the optical signals of each detection region may be acquired by obtaining the images of all the detection regions may be acquired, and analyzing color, brightness and/or the like of a region corresponding to the respective detection region of the image.

In step (S202), the reaction field is formed on the substrate with the reaction liquid.

The reaction liquid contains a sample, a primer set, amplification enzyme and the second marker substance.

The sample, primer set and amplification enzyme to be used may be any of those described above.

The second marker substance is a substance producing an optical signal upon the increase of the amplification product. The optical signal in, for example, light having a specific wavelength such as fluorescence or light emission. The second marker substance is, for example, a substance which emits fluorescence, and when binds to an amplification product, increase the fluorescent value in its detection region. Usable examples of the second marker substance are SYBRGreen, EvaGreen, SYTO, Berberine, Calcein, and HNB. Such a marker substance should preferably be contained in the reaction liquid at a concentration of 0.001 µM to 10 mM.

In addition to these ingredients, the reaction liquid may further contain magnesium, a salt, a substrate such as deoxynucleoside triphosphoric acid (dNTP), which is required to form a new polynucleotide using the primer as an origin of replication, a thickener as a reaction reagent, a buffer for pH adjustment, a surfactant, ion for enhancing the annealing specificity and/or ion which gives rise to a cofactor of the amplification enzyme, etc. When carrying out reverse transcription simultaneously, the reaction liquid may contain reverse transcriptase and a predetermined ingredient required for the amplification reaction, such as a substrate required therefor.

The reaction liquid described above is placed on the surface of the substrate, where the detection regions are disposed, to form one reaction field. The reaction field can be formed by any of the methods described above.

In step (S203), the reaction field is maintained in the isothermal amplification condition. This step can be carried out, for example, by a procedure similar to that of step (S3) described above.

In step (S204), the optical signal is detected by the respective optical sensors in a plurality of detection regions. The optical signal is the above-described optical signal produced from the second marker substance. The detection may be carried out, for example, by a procedure similar to the method described in step (S4), for example, may be carried out at the end point of the reaction or sequentially during the reaction.

In step (S205), it is determined whether an amplification product exists (positive) or does not exist (negative) in the vicinity of each of the detection regions based on the result of the detection. This step can be carried out, for example, by a procedure similar to that of step (S5) described above.

In this embodiment, the "vicinity" is defined, for example, as a region on the reaction field, located within such a distance from an edge of the optical sensor provided in the respective detection region is in a range of 0 to 10 mm.

In step (S206), the target nucleic acid is quantified from the number of positive detection regions, and/or the rise time of the optical signals. This step can be carried out, for example, by the same procedure as that of step (S6) described above.

According to the method described above, the target nucleic acid can be quantified simply at high sensitivity.

Figure 7:
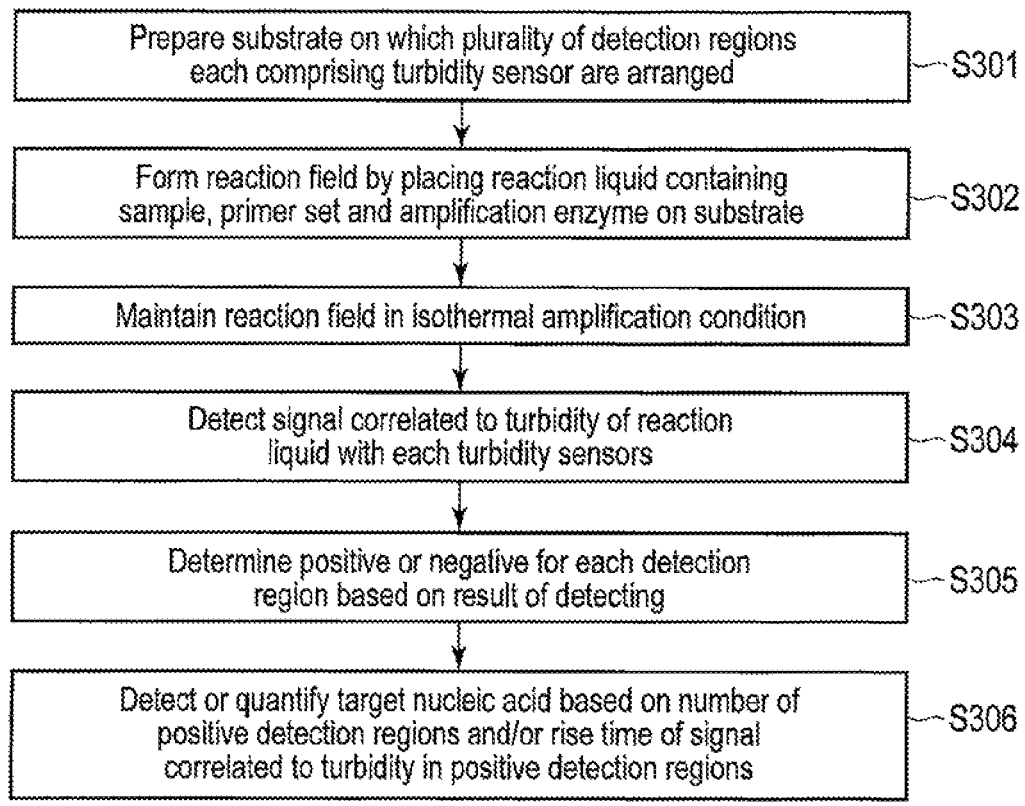
FIG. 7 is a flowchart showing an example of a nucleic acid detection or quantification method of the embodiment.

The Nucleic Acid Detection or Quantification Method Using Signal Correlated to Turbidity FIG. 7 is a flowchart schematically illustrating a nucleic acid detection or quantification method using a signal correlated to turbidity as the detection signal.

The method comprises: (S301) preparing a substrate on which a plurality of detection regions each comprising a turbidity sensor are arranged; (S302) forming one reaction field by placing, on the substrate, a reaction liquid containing a sample, a primer set for isothermally amplifying the first sequence to obtain an amplification product, and an amplification enzyme; (S303) maintaining the reaction field in an isothermal amplification condition; (S304) detecting a detection signal correlated to turbidity with each of the turbidity sensors; (S305) determining whether an amplification product exists in a vicinity (positive) or an amplification product does not exist (negative) for each of the plurality of detection regions, based on the result of the detecting; and (S306) detecting or quantifying a target nucleic acid based on the number of positive detection regions and/or the rise time of the signal correlated to the turbidity in each of the positive detection regions.

In step (S301), a substrate on which a plurality of detection regions each comprising a turbidity sensor are arranged, is prepared.

As the substrate, for example, any one of those shown in FIGS. 2 and 3, which comprise turbidity sensors respectively in the detection regions, can be used. The turbidity sensors should just be of any conventionally known type can detect a signal correlated to turbidity. The signal correlated to turbidity is a signal correlated to the turbidity of a reaction liquid, which can estimate the turbidity, that is, for example, the color of the reaction liquid, the intensity of transmitted light or intensity of dispersion light when light is applied to the reaction liquid, etc. For example, the turbidity sensors are each an element which detects signal correlated to turbidity and convert it into an electric signal. The turbidity sensors are arranged so to be able to detect the respective signals.

As the substrate, any one of those illustrated in FIGS. 2 and 3, in which, for example, a plurality of detection regions are each formed from a light-transmitting material. The light-transmitting material is, for example, a resin. With this structure, the signals correlated to turbidity can be detected, for example, by turbidity sensors separated from the substrate. Or the signals correlated to the turbidity of these detection regions may be acquired by obtaining the images of the detection regions and analyzing the color, brightness, etc., of a region equivalent to the detection region of each image.

In step (S302), the reaction field is formed on the substrate with the reaction liquid.

The reaction liquid contains a sample, a primer set and amplification enzyme.

The sample, primer set and amplification enzyme may be any one of those described above.

In addition to these ingredients, the reaction liquid may further contain magnesium, a salt, a substrate such as deoxynucleoside triphosphoric acid (dNTP), which is required to form a new polynucleotide using the primer as an origin of replication, a thickener as a reaction reagent, a buffer for pH adjustment, a surfactant, ion for enhancing the annealing specificity and/or ion which gives rise to a cofactor of the amplification enzyme, etc. When carrying out reverse transcription simultaneously, the reaction liquid may contain a reverse transcriptase and a predetermined ingredient required for the amplification reactions, such as a substrate required therefor.

The reaction liquid described above is placed on the surface of the substrate, where the detection regions are disposed, to form one reaction field. The reaction field can be formed by any of the methods described above.

In step (S303), the reaction field is maintained in the isothermal amplification condition. This step can be carried out, for example, by a procedure similar to that of step (S3) described above.

In step (S304), the signal correlated to turbidity is detected with the respective turbidity sensor in a plurality of detection regions. The detection of the signals correlated to turbidity may be carried out, for example, by a procedure similar to the method described in step (S4), for example, may be carried out at the end point of the reaction or sequentially during the reaction.

In step (S305), it is determined whether an amplification product exists (positive) or does not exist (negative) in the vicinity of each of the detection regions based on the result of the detection. This step can be carried out, for example, by a procedure similar to that of step (S5) described above. In this embodiment, the "vicinity" is defined, for example, as a region on the reaction field, located within such a distance from an edge of a plurality of detection regions is in a range of 0 to 10 mm.

In step (S306), the target nucleic acid is quantified from the number of positive detection regions, and/or the rise time of the signals correlated to turbidity. This step can be carried out, for example, by the same procedure as that of step (S6) described above.

According to the method described above, the target nucleic acid can be quantified simply at high sensitivity.

Chip

According to a further embodiment, there is provided a chip to quantify and detect a target nucleic acid in a sample. The chip includes a substrate and a plurality of detection regions disposed in one space on one surface of the substrate. The distance between two adjacent detection regions, that is, the closest interval between two detection regions adjacent to each other from an end of one detection region to a corresponding end of the other detection region may be 0.1 mm or more, 1 mm or more, or 0.1 mm to 10 mm. The interval should more preferably be 1 mm to 10 mm, in which case, the detection accuracy can be further improved.

In one embodiment of the chip, the substrate may comprises an electrode corresponding to each of the detection regions as described above. In another embodiment, the substrate may comprises an optical sensor corresponding to each of the detection regions as described above. In yet another embodiment, the substrate may comprises a turbidity sensor corresponding to each of the detection regions as described above.

The chip is a chip for detecting or quantifying target nucleic acid in the following manner. That is, a reaction liquid containing a sample, a primer set for isothermally amplifying the first sequence to obtain an amplification product, and amplification enzyme is placed on a substrate to form one reaction field which causes an amplification reaction. Then, the detection signal which varies with the increase of the amplification product are detected in each of the detection regions, each detection region is determined based on the result of the detection as to whether an amplification product exists (positive) or an amplification product does not exist (negative) in its vicinity. From the number of positive detection regions and/or the rise time of the detection signal in each of the positive detection regions, the target nucleic acid is detected or quantified.

The chip is a substrate in which any of these detection regions described above, for example, whose distance of two adjacent detection regions may be 0.1 mm or more, 1 mm or more, 0.1 mm to 10 mm, or 1 mm to 10 mm are disposed. For example, such substrates are substrates 1, 11, 21, 31 or 41 shown in FIG. 2 or 3. The chip may further comprise a cover member which covers the surface of the substrate, where the detection regions are disposed.

According to the chip described above, there is no need to dilute a sample or divide the reaction liquid, but with such a simple process of bringing the reaction liquid onto one continuous region on a substrate, the target nucleic acid can be detected at higher accuracy. For example, according to the chip of the embodiment, it is possible to detect, for example, 1 to $10^9$ copies/mL of target nucleic acid contained in the sample.

Assay Kit

According to the further embodiment, there is provided an assay kit to detect and quantify a target nucleic acid in a sample. The assay kit contains any one of the chips described above, a primer set for isothermally amplifying the first sequence to obtain an amplification product and an amplification reagent.

As the primer set, any one of those primer sets described can be used, for example. The amplification reagent contains, for example, amplification enzyme, a substrate such as deoxynucleoside triphosphoric acid (dNTP), a thickener as a reaction reagent, a buffer for pH adjustment, a surfactant, ion for enhancing the annealing specificity and/or ion which gives rise to a cofactor of the amplification enzyme, reverse transcriptase, or a combination of any of these. As the ingredients of these amplification reagents, any of those described above can be used.

The assay kit may further contain the first marker substance and/or the second marker substance described above.

According to the assay kit described above, there is no need to dilute a sample or divide the reaction liquid, but with such a simple process of bringing the reaction liquid onto one continuous region on a substrate, the target nucleic acid can be detected at higher accuracy. For example, according to the assay kit of the embodiment, it is possible to detect, for example, 1 to $10^9$ copies/mL of target nucleic acid contained in the sample.

Device for Detecting or Quantifying Nucleic Acid

Figure 8:
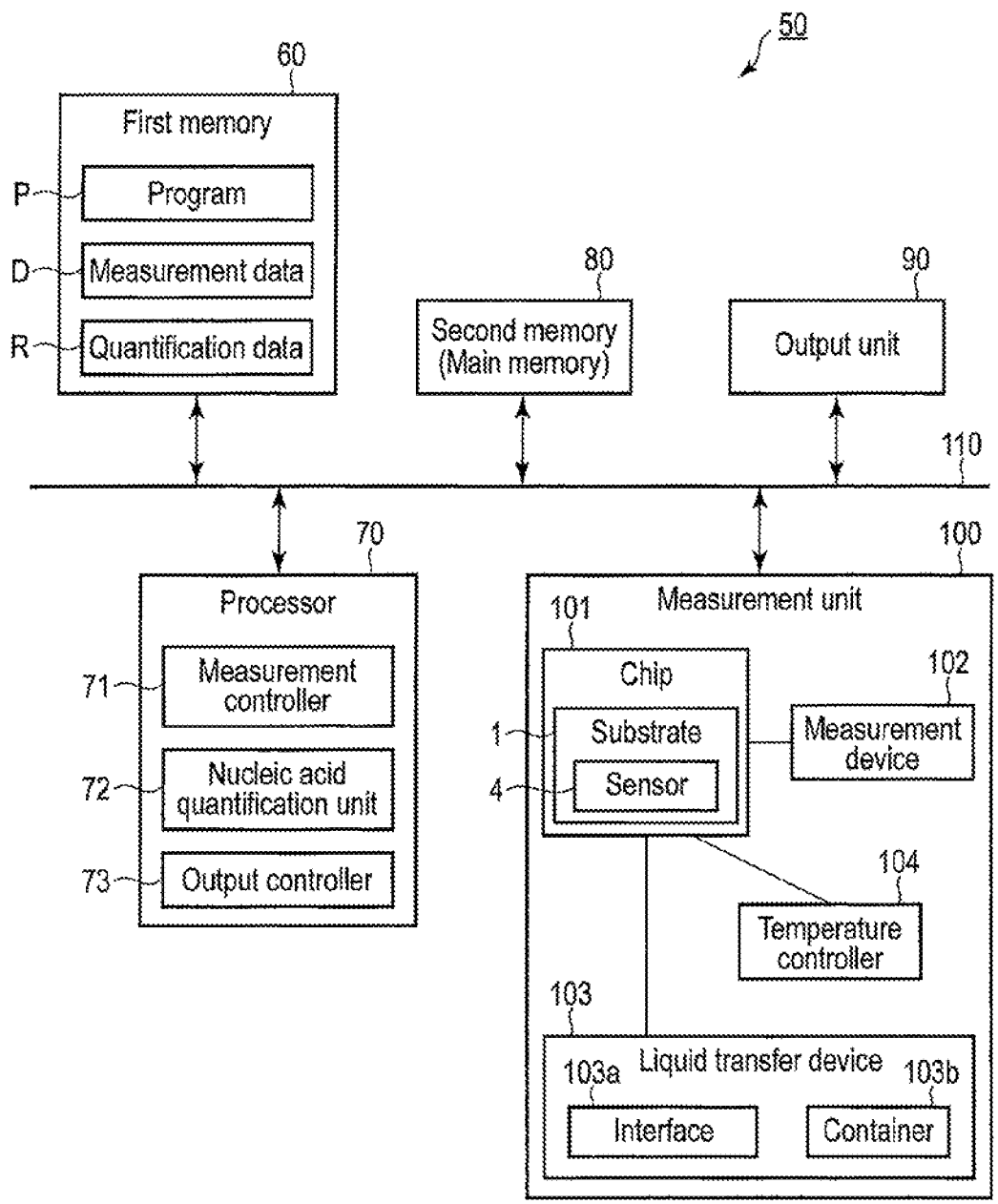

FIG. 8 shows an example of a device for detecting or quantifying nucleic acid (the nucleic acid detecting or quantifying device). FIG. 8 is a block diagram showing an example of a nucleic acid detecting or quantifying device 50. The nucleic acid detecting or quantifying device 50 comprises a first memory 60, a processor 70, a second memory 80, an output unit 90, a measurement unit 100 and the like. The first memory 60, processor 70, second memory 80, output unit 90 and measurement unit 100 are electrically connected to each other via a bus 110.

The first memory 60 is, for example, a hard disk, solid state drive (SSD), flash memory or the like and constitutes a storage area with the second memory 80.

The first memory 60 stores various types of software or data. The various types of software includes an operating system (OS), a data management program, various types of application programs, etc. The first memory 60 stores a program P.

The processor 70 executes the various types of software (programs) described above and controls the entire nucleic acid detecting or quantifying device 50. The processor 70 is, for example, a central processing unit (CPU), micro processing unit (MPU), digital signal processor (DSP) or the like.

The processor 70 executes the program P which is, for example, stored in the first memory 60 or read from the first memory 60 to the second memory 80, and thus functions as, for example, a measurement controller 71 or a nucleic acid quantification unit 72.

The measurement controller 71 is a control means which controls devices included in the measurement unit 100 (that is, for example, a chip 101, a measurement device 102, a liquid transfer device 103, a temperature controller 104, etc., which will be described later) and stores measurement data D obtained from the measurement unit 100 in the first memory 60.

The nucleic acid quantification unit 72 is a quantification means which quantifies a target nucleic acid in a sample based on measurement data D stored in the first memory 60. Further, the nucleic acid quantification unit 72 stores in the first memory 60 quantification data R which indicates a result of the quantification of the target nucleic acid in the sample.

The output controller 73 transmits the quantification data R stored in the first memory 60 to the output unit 90. Note that the output controller 73 may be included in the measurement controller 71 and/or the nucleic acid quantification unit 72.

The measurement data D and/or the quantification data R may be stored in the second memory 80.

The second memory 80 as the main memory is, for example, a random access memory (RAM) and is used as a work area or the like. The work area is used when the processor 70 executes various types of software.

The output unit 90 outputs quantification data R under the control of the output controller 73. The output unit 90 may be, for example, a display or printer.

The first memory 60 may be divided into two or more. The second memory 80 may be divided into two or more. Or the first memory 60 and the second memory 80 may be handled as one memory. The first memory 60, processor 70, second memory 60, output unit 90 and bus 110 may be built in an information processing device.

The measurement unit 100 includes the chip 101, measurement device 102, liquid transfer device 103 and temperature controller 104.

The chip 101 is disposed on the nucleic acid detecting or quantifying device 50 so as to be detachable therefrom. The chip 101 comprises a substrate 1 (see FIG. 2, part (a)) and a cover member (not shown) fixed to the substrate 1. The substrate 1 comprises, on one surface thereof, a plurality of detection regions each comprising, for example, a sensor 4 (see to FIG. 2, part (a)). The sensor 4 is, for example, an electrode when using an electric signal for detection of nucleic acid, or an optical sensor when using an optical signal, or a turbidity sensor when using a signal correlated to turbidity.

The following explanation is directed to an example case where the substrate 1 and the sensors 4 are contained in the chip 101 of the measurement unit 100. Alternatively, as shown in part (b) of FIG. 2 or parts (a) to (c) of FIG. 3, the substrate 11, 21, 31 or 41 comprising the sensors 16, 26, 36 or 46, respectively, or the like may be used in replace of the substrate 1 comprising the sensors 4.

A reaction field is formed as bringing the reaction liquid into the space by the substrate 1 and the cover member, and a predetermined amplification reaction occurs in the reaction field. The amplification reaction is, for example, the isothermal amplification reaction described above, or the like. An upper surface of the cover member is provided with an inlet for introducing a reaction liquid and an outlet for extracting the air and/or discharging the reaction liquid.

The measurement device 102 is electrically connected to the sensors 4 included in the chip 101, and is a measurement means to receive detection signals transmitted from the sensors 4. When the sensors 4 are each an electrode, the measurement device 102 can apply voltage to the electrode of the sensor 4 to receive the detection signal transmitted from the sensor 4. The measurement device 102 produces the measurement data D based on the detection signal received under the control of the measurement controller 71. The measurement data D include, for example, digital values and the like, indicating the presence/absence, intensity and/or detection time of the detection signals obtained in the sensor 4.

The liquid transfer device 103 is a liquid transfer means to send and/or extract the reaction liquid to/from the chip 101. The liquid transfer device 103 comprises, for example, an interface 103a with the chip 101 and a container 103b to contain a liquid such as a reaction liquid. The liquid transfer device 103 sends the liquid in the container 103b into the chip 101 via the interface 103a under the control of the measurement controller 71 in accordance with necessity.

Note that the nucleic acid detecting or quantifying device 50 may not necessarily comprise a liquid transfer device 103. In this case, the reaction liquid is transferred to or extracted from the chip 101 while the chip 101 is removed from the nucleic acid detecting or quantifying device 50 by a liquid transfer device separate from the nucleic acid detecting or quantifying device 50.

The temperature controller 104 is a temperature controlling means to control the temperature of the chip 101 under the control of the measurement controller 71. The temperature controller 104 may comprise, for example, a heater or a Peltier element.

Note that the nucleic acid detecting or quantifying device 50 may not necessarily comprise a temperature controller 104. In this case, the temperature of the chip 101 may be controlled by a temperature controller separate from the nucleic acid detecting or quantifying device 50.

Further, at least one of the processor 70, first memory 60, second memory 80 and output units 90 may be included in the measurement unit 100. In this case, at least one of the processor 70, first memory 60, second memory 80 and output units 90 should preferably be contained in the measurement device 102.

Figure 9:
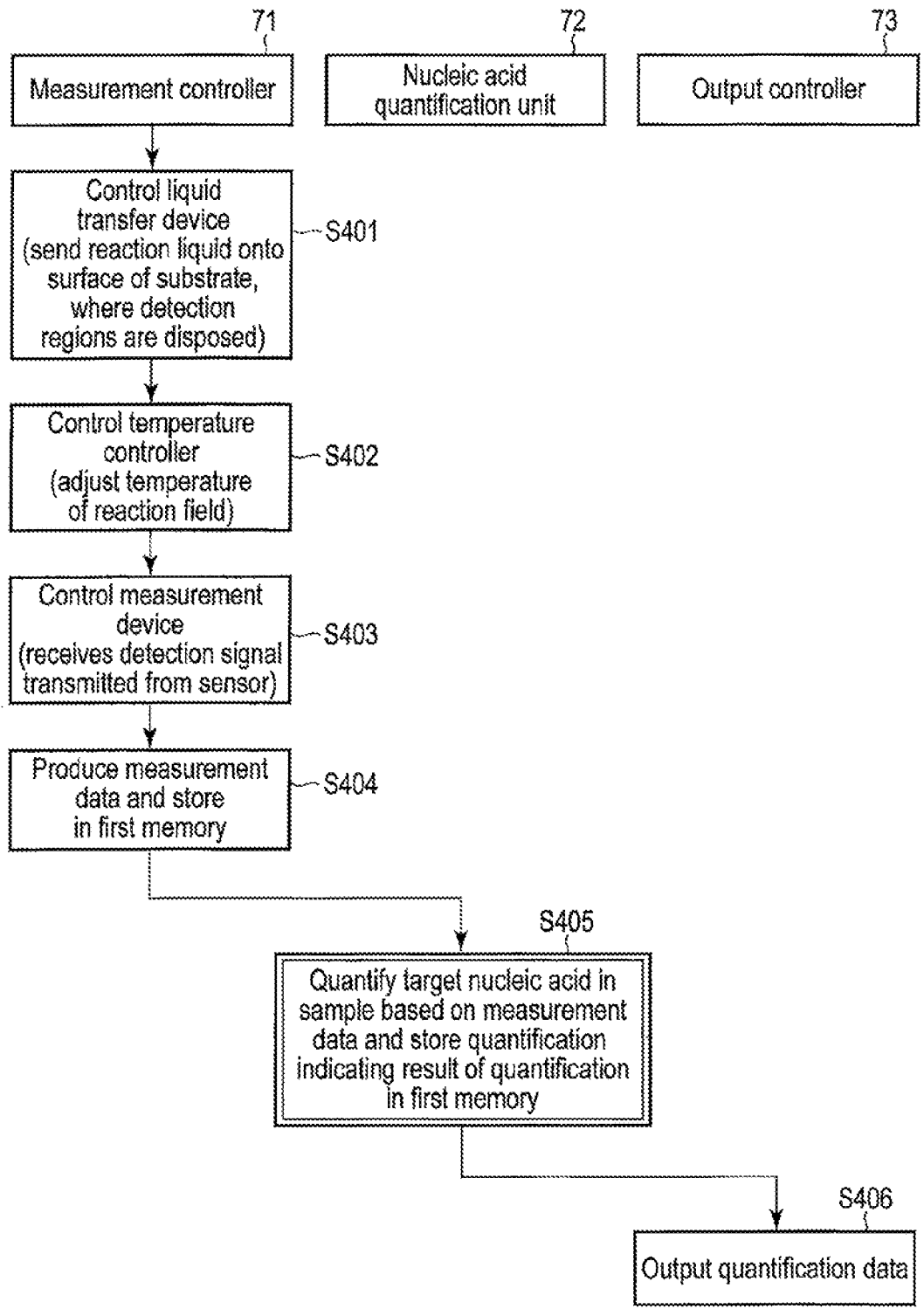
FIG. 9 is a flowchart showing an example of a nucleic acid detecting process by the device for detecting or quantifying nucleic acid of the embodiment.

The nucleic acid detection by the nucleic acid detecting or quantifying device 50 described above can be carried out as follows, for example, by the procedure shown in FIG. 9. FIG. 9 is a flowchart showing an example of the nucleic acid detection treatment using the nucleic acid detecting or quantifying device 50.

The operator loads the chip 101 on the measurement unit 100 in advance by insertion or the like. Further, let us suppose that the container 103b of the liquid transfer device 103 is filled with a reaction liquid in advance. Then, for example, with the operation by the operator, the nucleic acid detection quantification treatment by the nucleic acid detecting or quantifying device 50 is started. In the nucleic acid detection quantification treatment, the measurement controller 71 executes the treatments of steps (S401) to (S404), the nucleic acid quantification unit 72 executes the treatment of step (S405), and the output controller 73 executes the treatment of step (S406).

In step (S401), the liquid transfer device 103 sends the reaction liquid in the container 103b, under the control of the measurement controller 71, onto the surface of the substrate 1 of the chip 101, where a plurality of detection regions are disposed.

In step (S402), the temperature controller 104 adjusts the temperature of the reaction field under the control of the measurement controller 71. When the reaction field is maintained at the isothermal amplification condition, the isothermal amplification reaction is started in the reaction field.

In step (S403), the measurement device 102 receives a detection signal transmitted from the sensor 4 under the control of the measurement controller 71.

In step (404), the measurement controller 71 produces measurement data D from the detection signal received by the measurement device 102 and stores the measurement data D thus obtained in the first memory 60.

In step (S405), the nucleic acid quantification unit 72 reads the measurement data D from the first memory 60, and quantifies the target nucleic acid in the sample based on the measurement data D thus read. Details of the treatment of the nucleic acid quantification unit 72 will be described later with reference to FIG. 10. Note that the measurement data D may be stored in the second memory 80. Further, the nucleic acid quantification unit 72 stores the quantification data R indicating the result of the quantification of the target nucleic acid in the first memory 60.

In step (S406), the output controller 73 reads quantification data R from the first memory 60, and outputs it via the output unit 90. More specifically, the quantification data R may be output, for example, to a display or a printer.

Figure 10:
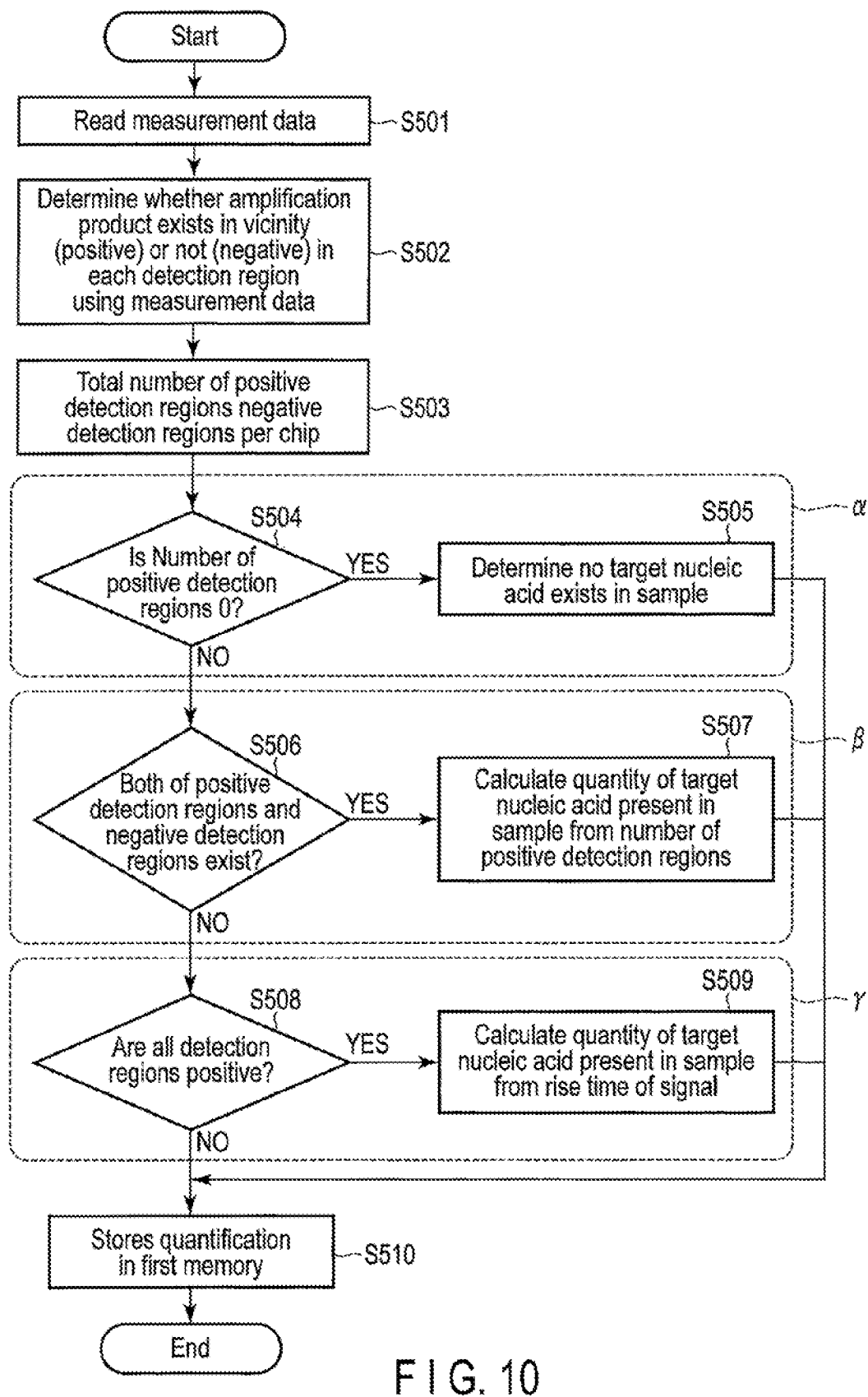
FIG. 10 is a flowchart showing an example of processing of a nucleic acid quantification unit of the embodiment.

FIG. 10 is a flowchart showing an example of treatment of the nucleic acid quantification unit 72. FIG. 10 corresponds to the treatment of the step (S405) of FIG. 9 executed by the nucleic acid quantification unit 72.

The nucleic acid quantification unit 72 executes the following treatments of steps (S501) to (S503).

In step (S501), the quantification means of the nucleic acid quantification unit 72 reads the measurement data D stored in the first memory 60 or the second memory 80 in step (S404).

In step (S502), the nucleic acid quantification unit 72 detects data contained in the measurement data D, that is, for example, temporal increase/decrease and/or rise time of the signal value received from the sensor 4, and thus determines whether an amplification product exists in a vicinity (positive) or an amplification product does not exists in a vicinity (negative) in each detection region.

In step (S503), the nucleic acid quantification unit 72 totals the number of positive detection regions and the number of negative detection regions per chip.

Next, the nucleic acid quantification unit 72 calculates, in three steps ($\alpha$) to ($\gamma$) described below, the quantity of the target nucleic acid present in the sample based on the number of the detection regions exhibiting to be positive.

In step ($\alpha$), if it is judged that the number of positive detection regions is 0 (step (S504)), the nucleic acid quantification unit 72 determines that no target nucleic acid exists in the sample (step (S505)).

In step ($\beta$), if it is judged that both of positive detection regions and negative detection regions exist (step (S506)), the nucleic acid quantification unit 72 calculates the quantity of the target nucleic acid present in the sample from the number of the positive detection regions, for example, by the above-described statistical method (step (S507)).

In process ($\gamma$), if it is judged that all the detection regions exhibit to be positive (step (S508)), the nucleic acid quantification unit 72 compares the quantity of standard sample nucleic acid and a predetermined calibration curve of the rise time of the signal as described above, to calculate out the quantity of the target nucleic acid present in the sample (step (S509)).

Further, in step (510), the nucleic acid quantification unit 72 stores the quantification data R indicating the quantification result of the target nucleic acid obtained by the above-described steps ($\alpha$) to ($\gamma$) in the first memory 60.

The nucleic acid detecting or quantifying device according to the embodiment can detect or quantify target nucleic acid in a simple manner with higher accuracy than the conventional techniques. Further, according to the nucleic acid detecting or quantifying device, it is possible to conduct the examination of the target nucleic acid in a shorter time than that of the conventional techniques.

EXAMPLES

Example 1

The time variations of the rise times of the current and potential in reaction liquids containing different numbers of copies of amplification product were examined using substrates comprising an array electrode.

Manufacture of Substrate

A flow channel having a width and a height (=1 mm×1 mm) was provided on a glass surface of Pyrex (registered trademark) (d=0.8 mm), and thus a substrate was formed. Then, thin film of titanium (500 nm) and gold (2,000 nm) were formed on a bottom of the flow channel and then selectively etched using a pattern of resist AZP4620 as a mask. Thus, eight gold/titanium electrodes (9-200 μm) (working electrodes) were formed. For every two active electrodes, a reference electrode and a counter electrode were formed to corresponding thereto.

Preparation of Reaction Liquid

Reaction liquids were prepared, which respectively contain 0 copy, $10^2$ copies, $10^3$ copies, $10^4$ copies and $10^5$ copies and $10^6$ copies of an artificial sequence (1 μL) of parvovirus (shown in TABLE 1 as SEQ ID NO: 1), F3 primer (SEQ ID NO: 2), B3 primer (SEQ ID NO: 3), FIP primer (SEQ ID NO: 4), BIP primer (SEQ ID NO: 5) and Lb primer (SEQ ID NO: 6) as a LAMP primer shown in TABLE 2, RuHex (25 μM), KCl (60 mM), magnesium ion (8 mM), ammonium ion (10 mM), betaine (0.8 M), dNTPs (1.4 mM each) and polymerase (GspSSD) (8 units).

TABLE 1

VP gene of Parvo virus (SEQ ID NO: 1)
AAACGCTAATACGACTCACTATAGGGCGATCTACGGGTACTTTCAATAAT

CAGACGGAATTTAAATTTTTGGAAAACGGATGGGTGGAAATCACAGCAAA

TABLE 1-continued

VP gene of Parvo virus

```
CTCAAGCAGACTTGTACATTTAAATATGCCAGAAAGTGAAAATTATAGAA
GAGTGGTTGTAAATAATTTGGATAAAACTGCAGTTAACGGAAACATGGCT
TTAGATGATACTCATGCACAAATTGTAACACCTTGGTCATTGGTTGATGC
AAATGCTTGGGGAGTTTGGTTTAATCCAGGAGATTGGCAACTAATTGTTA
ATACTATGAGTGAGTTGCATTTAGTTAGTTTTGAACAAGAAATTTTTAAT
GTTGTTTTAAAGACTGTTTCAGAATCTGCTACTCAGCCACCAACTAAAGT
TTATAATAATGATTTAACTGCATCATTGATGGTTGCATTAGATAGTAATA
ATACTATGCCATTTACTCCAGCAGCTATGAGATCTGAGACATTGGGTTTT
TATCCATGGAAACCAACCATACCAACTCCATCGAGATATTATTTTCAATG
GGATAGAACATTAATACCATCTCATACTGGAACTAGTGGCACACCAACAA
ATATATACCATGGTACAGATCCAGATGATGTTCAATTTTATACTATTGAA
AATTCTGTGCCAGTACACTTACTAAGAACAGGTGATGAATTTGCTACAGG
AACATTTTTTTTGATTGTAAACCATGTAGACTAACACATACATGGCAAA
CAAATAGAGCATTGGGCTTACCACCATTTCTAAATTCTTTGCCTCAAGCT
GAAGGAGGTACTAACTTTGGTTATATAGGAGTTCAACAAGATAAAAGACG
TGGTGTAACTCAAATGGGAAATACAAACTATATTACTGAAGCTACTATTA
TGAGACCAGCTGAGGTTGGTTATAGTGCACCATATTATTCTTTTGAGGCG
TCTACACAAGGGCCATTTAAAACACCCTTCCCTTTAGTGAGGGTTAATAA
```

TABLE 2

| SEQ ID NO | | Sequence |
|---|---|---|
| 2 | F3 | GAGATATTATTTTCAATGGCATAGAAC |
| 3 | B3 | CAATGCTCTATTTGTTTGCCATG |
| 4 | FIP | GAACATCATCTGGATCTGTACCAACCATCTCATACTGGAACTACTGGC |
| 5 | BIP | CTGTGCCAGTACACTTACTAAGAGTGTTAGTCTACATGGTTTACAATC |
| 6 | Lb | ACAGGTGATGAATTTGCTACAGG |

LAMP Amplification Reaction

These reaction liquids were brought onto the surface of the substrate comprising electrodes, and they were warmed isothermally at 67° C., to start the amplification reactions. As the amplification reactions proceeded, the electric signals were measured by the LSV method (sweep rate: 0.5 V/s). A detection region with an electrode which detected a signal of 1 nA/min or higher was detected within 60 minutes after the reaction started was determined as "positive", and a detection region with an electrode of less than 1 nA/min was determined as "negative". The results are shown in FIG. 11. Part (a) of FIG. 11 shows the relationship between the initial number of templates and the positive rate, and part (b) shows the relationship between the initial number of templates and the increase time (rise time) of the current value.

Under the conditions of the initial number of templates of $10^3$ copies or more, the positive rate was 100%. Further, on this condition, the initial number of templates and the increase time of the current value have a linear relation with respect to each other. Here, the correlation coefficient ($R^2$) indicated 0.93 and the inclination indicated −2.2. From this result, it was suggested that when the initial number of templates was $10^3$ copies or more, the number of initial templates can be quantified from the current value.

On the other hand, under the conditions of the initial number of templates of $10^2$ copies or less, negative detection regions existed, and the positive rate was 88% for $10^2$ copies and 25% for $10^1$ copies. From this result, when less than $10^3$ copies, it was suggested that the initial number of templates can be quantified from the positive rate.

Example 2

Using the results of Example 1, a calculation table was created to estimate the concentration of the target nucleic acid from the positive rate for the case where the target nucleic acid of less than $10^3$ copies in a sample was to be quantified using the substrate of Example 1.

Calculation of Reaction Volume Per Electrode

In order to estimate the concentration of target nucleic acid from the positive rate, the most probable number method which uses the formula below was used to estimate a most probable number (estimated quantity of target nucleic acid: MPN).

$$\text{MPN} = 1/m \times 2.303 \times \log((\text{number of detection regions})/(\text{number of negatives})) \quad \text{Formula 3}$$

where m is a reaction volume (μL) per electrode.

The reaction volume, which is a parameter necessary to calculate the most probable number was calculated from the result of Example 1.

When Formula 3 is transformed, we obtain
m=2.303×log((total number of electrodes)/(number of negatives))/MPN. When m is obtained from the result of $10^2$ copies/50 μL of Example 1, i.e., 2 copies/μL, it was 1.03 μL. When m is obtained from the result of $10^1$ copies/50 μL of Example 1, i.e., 0.2 copies/μL, it was 1.44 μL. An average of these two values is taken, and m=1.2 μL was used for the calculation table. The most probable number was calculated using an MPN calculator.

Similarly, a substrate comprising 80 electrodes was examined and a calculation table was created.

The calculation table thus created is shown in TABLE 3.

TABLE 3

Calculation table for quantification of target nucleic acid using MPN method

| Positive rate (%) | Estimated Conc.* (Copies/μL) | 95%-reliable zone (Copies/μL) | |
|---|---|---|---|
| | | n = 8 | n = 80 |
| 100 | — | >1.7 | >3.7 |
| 87.5 | 1.7 | 0.7-4.2 | 1.3-2.3 |
| 75 | 1.2 | 0.5-2.8 | 0.9-1.5 |
| 62.5 | 0.8 | 0.3-2.0 | 0.6-1.1 |
| 50 | 0.6 | 0.2-1.6 | 0.4-0.8 |
| 37.5 | 0.4 | 0.1-1.2 | 0.3-0.6 |
| 25 | 0.2 | 0.1-1.0 | 0.2-0.4 |
| 12.5 | 0.1 | 0.0-0.8 | 0.1-0.2 |
| 0 | — | <0.1 | <0.0 |

*Estimated concentration (/μL) = 1/1.2 μL × 2.303 × log((number of electrodes(n))/(number of negatives))

It has been clarified from the above-described tests that according to the method of the embodiment, a low-concentration target nucleic acid can be quantified from the positive rate without preparing a calibration curve. Further, with an increased number of electrodes, the accuracy of the quantification of a low-concentration target nucleic acid can be greatly improved. Moreover, when the sample is not diluted, the MPN method can be adapted for the quantification of low-concentration target nucleic acids, whereas middle- to high-concentration (≥$10^2$ copies/500 μL) target nucleic acids can be quantified from the rise time of the signal by preparing a calibration curve in advance.

Example 3

The optimal distance between electrodes was examined using the substrate of Example 1.

The flow channel had a width×height=1 mm×1 mm, and therefore it was considered from the reaction volume calculated in Example 2 that the electrodes can detect signals from the region in which the distance from the edge of the electrode is within about 0.6 mm. In order to increase the degree of integration, the interval between electrodes should preferably be shorter, but if excessively short, an amplification product produced from one target nucleic acid may be detected by a plurality of electrodes. Thus, it has been clarified that in order to avoid this, the distance from one end of an electrode to an and of an adjacent electrode thereto should necessarily be at least 1 mm or more.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A device for detecting or quantifying one kind of target nucleic acid, the device comprising a measurement unit, wherein
the measurement unit includes a chip and a measurement device, wherein
the chip comprises a substrate, of which one surface comprises a plurality of detection regions without nucleic acid probes, and a cover member which covers the surface of the substrate, wherein a groove is positioned between the surface of the substrate and the cover member, and the plurality of detection regions are positioned in the groove,
the measurement device is electrically connected to the plurality of detection regions, receiving a detection signal from the detection region, and
the groove is configured to bring a reaction liquid containing the target nucleic acid.

2. The device of Claim 1, further comprising a memory and a processor, which are electrically connected with each other and the measurement unit wherein
the processor is configured to:
read a program for controlling the measurement unit from the memory,
produce measurement data from the detection signal with the measurement data including a rise time of the detection signal,
store the measurement data in the memory,
quantify the target nucleic acid in a sample based on the measurement data,
read the measurement data stored in the memory;
determine whether each of the plurality of the detection regions is a positive region where amplified produces exist in the vicinity or a negative region where no amplified products exist in the vicinity,
wherein
a region among the plurality of detection regions where: the rise time of the detection signal is shorter than that in the other detection regions is determined to be the positive region, and
a region among the plurality of detection regions where the rise time of the detection signal is longer than that in the other detection regions is determined to be the negative region;
total the number of the positive and the number of the negative regions;

determine, when the number of the detection regions exhibiting the positive value is 0, that the target nucleic acid does not exist in the sample;

calculate the quantity of the target nucleic acid present in the sample, when both of the positive regions and the negative regions exist, from the number of the positive regions exhibiting; and calculate the quantity of the target nucleic acid in the sample, when all the detection regions are the positive regions, from the rise time of the signal and store the calculated value of the quantity of the target nucleic acid in thy; sample in the memory.

3. The device of claim 2, further comprising a liquid transfer unit, which includes a container for storing liquid, sending the liquid stored in the container to the chip, and/or extracting it therefr©m under the control of the processor.

4. The device of claim 2, further comprising a temperature control unit controlling the temperature of the chip under the control of the processor.

\* \* \* \* \*